US006461837B1

(12) United States Patent
Yaver et al.

(10) Patent No.: US 6,461,837 B1
(45) Date of Patent: Oct. 8, 2002

(54) METHODS FOR PRODUCING A POLYPEPTIDE USING A CONSENSUS TRANSLATIONAL INITIATOR SEQUENCE

(75) Inventors: Debbie S. Yaver, Davis; Daniel Alan Bellini, Woodland, both of CA (US)

(73) Assignee: Novozymes Biotech, Inc., Davis, CA (US)

( * ) Notice: Subject to any disclaimer, the term of this patent is extended or adjusted under 35 U.S.C. 154(b) by 0 days.

(21) Appl. No.: 09/717,847

(22) Filed: Nov. 20, 2000

Related U.S. Application Data

(63) Continuation-in-part of application No. 09/451,503, filed on Nov. 30, 1999, now abandoned.

(51) Int. Cl.$^7$ ................... C12P 21/06; C12N 15/09; C12N 15/80; C12N 1/15; C12N 1/19
(52) U.S. Cl. ............... 435/69.1; 435/69.2; 435/69.4; 435/320.1; 435/254.11; 435/254.2; 435/254.3; 435/254.7; 435/198; 435/205; 435/207; 435/208; 435/209; 536/23.1; 536/24.1
(58) Field of Search ................ 536/23.1, 24.1; 435/69.1, 69.2, 69.4, 320.1, 254.11, 254.2, 254.3, 254.7, 198, 205, 207, 208, 209

(56) References Cited

PUBLICATIONS

Kozak, 1981, *Nucleic Acids Research* 9: 5233–5252.
Kozak, 1987, *Molecular Cell Biology* 7: 3438–3445.
Kozak, 1986, *Proceedings of the National Academy of Sciences USA* 83: 2850–2854.

*Primary Examiner*—David Guzo
*Assistant Examiner*—Katherine F Davis
(74) *Attorney, Agent, or Firm*—Robert L. Starnes

(57) ABSTRACT

The present invention relates to methods for producing a polypeptide, comprising: (a) cultivating a fungal host cell in a medium conducive for the production of the polypeptide, wherein the fungal host cell comprises a first nucleic acid sequence encoding the polypeptide operably linked to a second nucleic acid sequence comprising a consensus translational initiator sequence foreign to the nucleic acid sequence; and (b) isolating the polypeptide from the cultivation medium. The present invention also relates to the isolated consensus translational initiator sequences and to constructs, vectors, and fungal host cells comprising the consensus translational initiator sequences operably linked to nucleic acid sequences encoding polypeptides.

25 Claims, 13 Drawing Sheets

SEQUENCE LISTING

```
<160> NUMBER OF SEQ ID NOS: 48

<210> SEQ ID NO 1
<211> LENGTH: 10
<212> TYPE: DNA
<213> ORGANISM: Aspergillus oryzae
<220> FEATURE:
<223> OTHER INFORMATION: N is A, C, G, or T; Y is C or T; and H is A, C,
      or T

<400> SEQUENCE: 1 nycnnhcacc                                                              10

<210> SEQ ID NO 2
<211> LENGTH: 13
<212> TYPE: DNA
<213> ORGANISM: Aspergillus oryzae

<400> SEQUENCE: 2
gtccttcacc atg                                                          13

<210> SEQ ID NO 3
<211> LENGTH: 13
<212> TYPE: DNA
<213> ORGANISM: Aspergillus oryzae

<400> SEQUENCE: 3
gtcctccacc atg                                                          13

<210> SEQ ID NO 4
<211> LENGTH: 13
<212> TYPE: DNA
<213> ORGANISM: Aspergillus oryzae

<400> SEQUENCE: 4
gtcctacacc atg                                                          13

<210> SEQ ID NO 5
<211> LENGTH: 24
<212> TYPE: DNA
<213> ORGANISM: Aspergillus oryzae

<400> SEQUENCE: 5
atgcatctgg aaacgcaacc ctga                                              24

<210> SEQ ID NO 6
<211> LENGTH: 24
<212> TYPE: DNA
<213> ORGANISM: Aspergillus oryzae

<400> SEQUENCE: 6
atgcattcta cgccaggacc gagc                                              24

<210> SEQ ID NO 7
<211> LENGTH: 21
<212> TYPE: DNA
<213> ORGANISM: Aspergillus oryzae

<400> SEQUENCE: 7
tggtgtacag gggcataaaa t                                                 21

<210> SEQ ID NO 8
```

-continued

```
<210> SEQ ID NO 8
<211> LENGTH: 34
<212> TYPE: DNA
<213> ORGANISM: Aspergillus oryzae

<400> SEQUENCE: 8
atttaaatcc agttgtgtat atagaggatt gtgg                              34

<210> SEQ ID NO 9
<211> LENGTH: 30
<212> TYPE: DNA
<213> ORGANISM: Aspergillus oryzae

<400> SEQUENCE: 9
atttaaatga tgaggagctc ccttgtgctg                                   30

<210> SEQ ID NO 10
<211> LENGTH: 29
<212> TYPE: DNA
<213> ORGANISM: Aspergillus oryzae

<400> SEQUENCE: 10
ttaattaact agagtcgacc cagccgcgc                                    29

<210> SEQ ID NO 11
<211> LENGTH: 24
<212> TYPE: DNA
<213> ORGANISM: Aspergillus oryzae

<400> SEQUENCE: 11
atgcatctgg aaacgcaacc ctga                                         24

<210> SEQ ID NO 12
<211> LENGTH: 24
<212> TYPE: DNA
<213> ORGANISM: Aspergillus oryzae

<400> SEQUENCE: 12
atgcattcta cgccaggacc gagc                                         24

<210> SEQ ID NO 13
<211> LENGTH: 13
<212> TYPE: DNA
<213> ORGANISM: Aspergillus oryzae

<400> SEQUENCE: 13
catttaaatg atg                                                     13

<210> SEQ ID NO 14
<211> LENGTH: 36
<212> TYPE: DNA
<213> ORGANISM: Aspergillus oryzae

<400> SEQUENCE: 14
ccacagaagg catttaattg atgaggagct cccttg                            36

<210> SEQ ID NO 15
<211> LENGTH: 36
<212> TYPE: DNA
<213> ORGANISM: Aspergillus oryzae

<400> SEQUENCE: 15
caagggagct cctcatcaat taaatgcctt ctgtgg                            36
```

```
<210> SEQ ID NO 16
<211> LENGTH: 36
<212> TYPE: DNA
<213> ORGANISM: Aspergillus oryzae

<400> SEQUENCE: 16
ccacagaagg catttaactg atgaggagct cccttg                          36

<210> SEQ ID NO 17
<211> LENGTH: 36
<212> TYPE: DNA
<213> ORGANISM: Aspergillus oryzae

<400> SEQUENCE: 17
caagggagct cctcatcagt taaatgcctt ctgtgg                          36

<210> SEQ ID NO 18
<211> LENGTH: 36
<212> TYPE: DNA
<213> ORGANISM: Aspergillus oryzae

<400> SEQUENCE: 18
ccacagaagg catttaagtg atgaggagct cccttg                          36

<210> SEQ ID NO 19
<211> LENGTH: 36
<212> TYPE: DNA
<213> ORGANISM: Aspergillus oryzae

<400> SEQUENCE: 19
caagggagct cctcatcact taaatgcctt ctgtgg                          36

<210> SEQ ID NO 20
<211> LENGTH: 21
<212> TYPE: DNA
<213> ORGANISM: Aspergillus oryzae

<400> SEQUENCE: 20
agagtgacta ggggcggaaa t                                          21

<210> SEQ ID NO 21
<211> LENGTH: 21
<212> TYPE: DNA
<213> ORGANISM: Aspergillus oryzae

<400> SEQUENCE: 21
ccggtgacat cgcccactcc a                                          21

<210> SEQ ID NO 22
<211> LENGTH: 16
<212> TYPE: DNA
<213> ORGANISM: Aspergillus oryzae

<400> SEQUENCE: 22
catttaaatg ttgatg                                                16

<210> SEQ ID NO 23
<211> LENGTH: 16
<212> TYPE: DNA
<213> ORGANISM: Aspergillus oryzae

<400> SEQUENCE: 23
catttaaatg ctgatg                                                16
```

```
<210> SEQ ID NO 24
<211> LENGTH: 16
<212> TYPE: DNA
<213> ORGANISM: Aspergillus oryzae

<400> SEQUENCE: 24
catttaaatg gtgatg                                                    16

<210> SEQ ID NO 25
<211> LENGTH: 21
<212> TYPE: DNA
<213> ORGANISM: Aspergillus oryzae

<400> SEQUENCE: 25
ggtccagaca actcccagaa c                                              21

<210> SEQ ID NO 26
<211> LENGTH: 21
<212> TYPE: DNA
<213> ORGANISM: Aspergillus oryzae

<400> SEQUENCE: 26
cgaggcgtgc gtagtaggtc t                                              21

<210> SEQ ID NO 27
<211> LENGTH: 50
<212> TYPE: DNA
<213> ORGANISM: Aspergillus oryzae

<400> SEQUENCE: 27
gcccgggatc gatgcatcta gatatctaga tgcatcgatc ccgggctgca               50

<210> SEQ ID NO 28
<211> LENGTH: 29
<212> TYPE: DNA
<213> ORGANISM: Aspergillus oryzae

<400> SEQUENCE: 28
ggaacgatgg acccggaagg tttaaaagc                                      29

<210> SEQ ID NO 29
<211> LENGTH: 13
<212> TYPE: DNA
<213> ORGANISM: Aspergillus oryzae

<400> SEQUENCE: 29
gggatccacc atg                                                       13

<210> SEQ ID NO 30
<211> LENGTH: 36
<212> TYPE: DNA
<213> ORGANISM: Aspergillus oryzae

<400> SEQUENCE: 30
ccccacagaa gggatccact atgaggagct cccttg                              36

<210> SEQ ID NO 31
<211> LENGTH: 36
<212> TYPE: DNA
<213> ORGANISM: Aspergillus oryzae

<400> SEQUENCE: 31
caagggagct cctcatagtg gatcccttct gtgggg                              36
```

<210> SEQ ID NO 32
<211> LENGTH: 36
<212> TYPE: DNA
<213> ORGANISM: Aspergillus oryzae

<400> SEQUENCE: 32
ccccacagaa gggatccatc atgaggagct cccttg            36

<210> SEQ ID NO 33
<211> LENGTH: 36
<212> TYPE: DNA
<213> ORGANISM: Aspergillus oryzae

<400> SEQUENCE: 33
caagggagct cctcatgatg gatcccttct gtgggg            36

<210> SEQ ID NO 34
<211> LENGTH: 36
<212> TYPE: DNA
<213> ORGANISM: Aspergillus oryzae

<400> SEQUENCE: 34
ccccacagaa gggatcctcc atgaggagct cccttg            36

<210> SEQ ID NO 35
<211> LENGTH: 36
<212> TYPE: DNA
<213> ORGANISM: Aspergillus oryzae

<400> SEQUENCE: 35
caagggagct cctcatggag gatcccttct gtgggg            36

<210> SEQ ID NO 36
<211> LENGTH: 36
<212> TYPE: DNA
<213> ORGANISM: Aspergillus oryzae

<400> SEQUENCE: 36
ccccacagaa gggatctacc atgaggagct cccttg            36

<210> SEQ ID NO 37
<211> LENGTH: 36
<212> TYPE: DNA
<213> ORGANISM: Aspergillus oryzae

<400> SEQUENCE: 37
caagggagct cctcatggta gatcccttct gtgggg            36

<210> SEQ ID NO 38
<211> LENGTH: 36
<212> TYPE: DNA
<213> ORGANISM: Aspergillus oryzae

<400> SEQUENCE: 38
ccccacagaa gggatctttt atgaggagct cccttg            36

<210> SEQ ID NO 39
<211> LENGTH: 36
<212> TYPE: DNA
<213> ORGANISM: Aspergillus oryzae

<400> SEQUENCE: 39

-continued caagggagct cctcataaaa gatcccttct gtgggg                36

<210> SEQ ID NO 40
<211> LENGTH: 36
<212> TYPE: DNA
<213> ORGANISM: Aspergillus oryzae

<400> SEQUENCE: 40
ccccacagaa gtccttcacc atgaggagct cccttg                36

<210> SEQ ID NO 41
<211> LENGTH: 36
<212> TYPE: DNA
<213> ORGANISM: Aspergillus oryzae

<400> SEQUENCE: 41
caagggagct cctcatggtg aaggacttct gtgggg                36

<210> SEQ ID NO 42
<211> LENGTH: 12
<212> TYPE: DNA
<213> ORGANISM: Aspergillus oryzae

<400> SEQUENCE: 42
ggatccacca tg                                          12

<210> SEQ ID NO 43
<211> LENGTH: 12
<212> TYPE: DNA
<213> ORGANISM: Aspergillus oryzae

<400> SEQUENCE: 43
ggatccacta tg                                          12

<210> SEQ ID NO 44
<211> LENGTH: 12
<212> TYPE: DNA
<213> ORGANISM: Aspergillus oryzae

<400> SEQUENCE: 44
ggatccatca tg                                          12

<210> SEQ ID NO 45
<211> LENGTH: 12
<212> TYPE: DNA
<213> ORGANISM: Aspergillus oryzae

<400> SEQUENCE: 45
ggatcctcca tg                                          12

<210> SEQ ID NO 46
<211> LENGTH: 12
<212> TYPE: DNA
<213> ORGANISM: Aspergillus oryzae

<400> SEQUENCE: 46
ggatctacca tg                                          12

<210> SEQ ID NO 47
<211> LENGTH: 12
<212> TYPE: DNA
<213> ORGANISM: Aspergillus oryzae

<400> SEQUENCE: 47

-continued

```
ggatctttta tg                                                          12

<210> SEQ ID NO 48
<211> LENGTH: 12
<212> TYPE: DNA
<213> ORGANISM: Aspergillus oryzae

<400> SEQUENCE: 48
tccttcacca tg                                                          12
```

METHODS FOR PRODUCING A POLYPEPTIDE USING A CONSENSUS TRANSLATIONAL INITIATOR SEQUENCE

CROSS-REFERENCE TO RELATED APPLICATION

This application is a continuation-in-part of pending U.S. application Ser. No. 09/451,503 filed on Nov. 30, 1999, now abandoned, which application is fully incorporated herein by reference.

BACKGROUND OF THE INVENTION

1. Field of the Invention

The present invention relates to methods for producing polypeptides. The present invention also relates to nucleic acid constructs, vectors, and host cells comprising consensus translational initiator sequences operably linked to nucleic acid sequences encoding polypeptides, and isolated consensus translational initiator sequences.

2. Description of the Related Art

The recombinant production of a heterologous protein in a fungal host cell, particularly a filamentous fungal cell such as Aspergillus, may provide for a more desirable vehicle for producing the protein in commercially relevant quantities.

Recombinant production of a heterologous protein is accomplished by constructing an expression cassette in which the DNA coding for the protein is placed under the expression control of a promoter, excised from a regulated gene, suitable for the host cell. The expression cassette is introduced into the host cell, usually by plasmid-mediated transformation. Production of the heterologous protein is then achieved by culturing the transformed host cell under inducing conditions necessary for the proper functioning of the promoter contained on the expression cassette.

Improvement of the recombinant production of proteins generally requires the availability of new regulatory sequences which are suitable for controlling the expression of the proteins in a host cell.

Kozak, 1981, *Nucleic Acids Research* 9: 5233–5252, proposed the following "consensus" sequence for initiation of translation in higher eukaryotes:

Aa Acc <u>AUG</u> G

In this sequence, referred to as a "consensus Kozak," the most highly conserved nucleotides are the purines, adenine (A) and guanine (G), shown in capital letters above. Mutational analysis confirmed that these two positions have the strongest influence on initiation (Kozak, 1987, *Molecular Cell Biology* 7: 3438–3445). Kozak also determined that alterations in the sequence upstream of the consensus Kozak can effect translation (Kozak, 1986, *Proceedings of the National Academy of Sciences USA* 83: 2850–2854).

It is an object of the present invention to provide improved methods for producing a polypeptide in a fungal host cell using consensus translational initiator sequences.

SUMMARY OF THE INVENTION

The present invention relates to methods for producing a polypeptide, comprising: (a) cultivating a fungal host cell in a medium conducive for the production of the polypeptide, wherein the fungal host cell comprises a first nucleic acid sequence encoding the polypeptide operably linked to a second nucleic acid sequence comprising a consensus translational initiator sequence foreign to the first nucleic acid sequence wherein the 3' end of the consensus translational initiator sequence is immediately upstream of the initiator codon of the first nucleic acid sequence, and the consensus translational initiator sequence comprises the sequence 5'-NYCNNHCACC-3' (SEQ ID NO. 1) wherein N is a nucleotide selected from the group consisting of adenine (A), guanine (G), cytosine (C), and thymine (T); Y is a cytosine (C) or thymine (T); and H is a nucleotide selected from the group consisting of adenine (A), cytosine (C), and thymine (T); and (b) isolating the polypeptide from the cultivation medium.

The present invention also relates to isolated consensus translational initiator sequences and to constructs, vectors, and fungal host cells comprising one or more of the consensus translational initiator sequences operably linked to a nucleic acid sequence encoding a polypeptide.

DETAILED DESCRIPTION OF THE INVENTION

Figure 1:
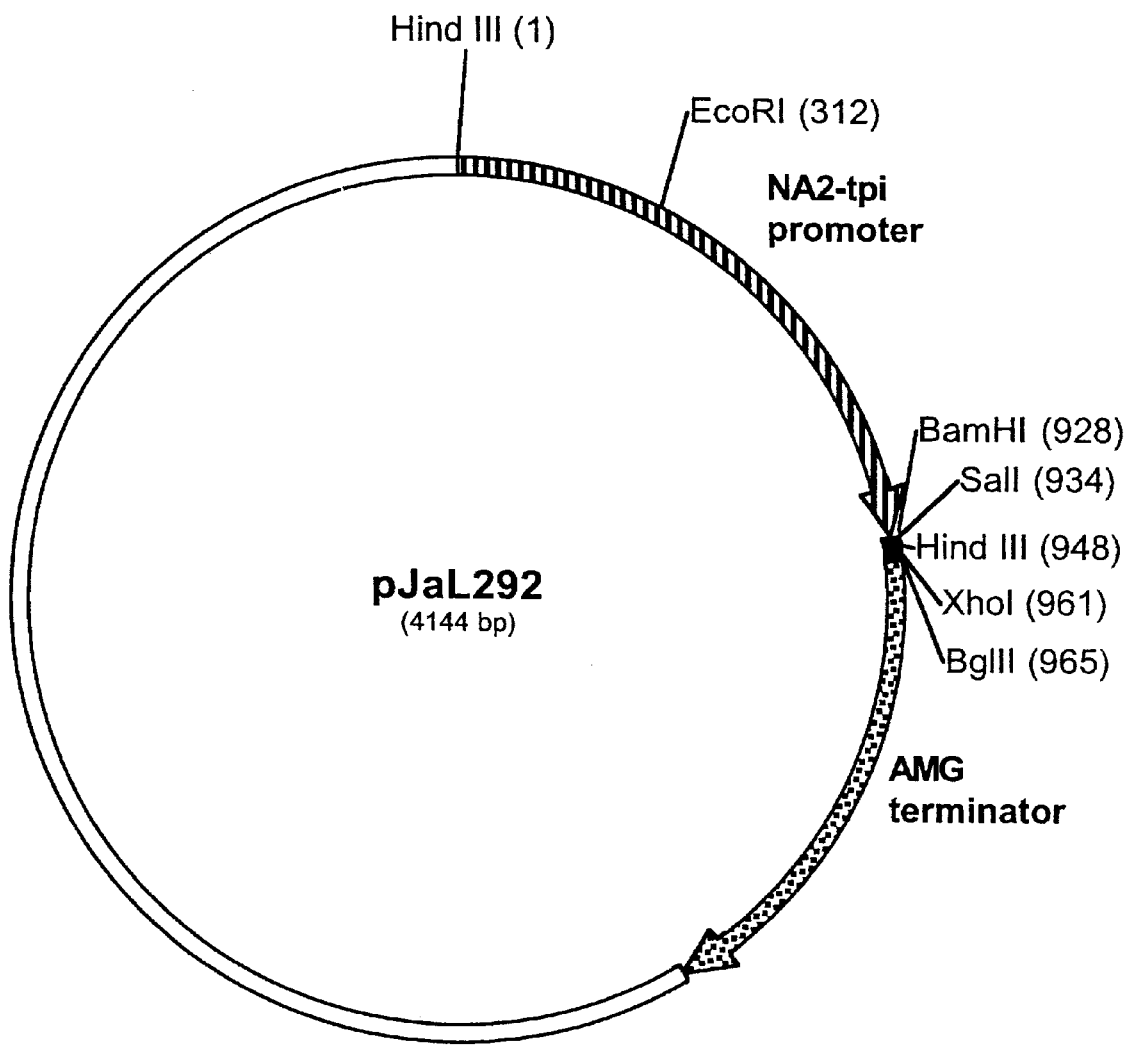
FIG. 1 shows a restriction map of pJaL292.

The present invention relates to methods for producing a polypeptide, comprising (a) cultivating a fungal host cell in a medium conducive for the production of the polypeptide, wherein the fungal host cell comprises a first nucleic acid sequence encoding the polypeptide operably linked to a second nucleic acid sequence comprising a consensus translational initiator sequence foreign to the first nucleic acid sequence; and (b) isolating the polypeptide from the cultivation medium.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of an enzyme product, or disappearance of an enzyme substrate.

In the methods of the present invention, the fungal cell preferably produces at least about 25% more, more preferably at least about 50% more, more preferably at least about 75% more, more preferably at least about 100% more, even more preferably at least about 200% more, most preferably at least about 300% more, and even most preferably at least about 400% more polypeptide relative to a fungal cell containing a non-consensus translational initiator sequence operably linked to a nucleic acid sequence encoding the polypeptide when cultured under identical production conditions.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989).

Consensus Translational Initiator Sequences

The term "translational initiator sequence" is defined herein as the ten nucleotides immediately upstream of the initiator or start codon of the open reading frame of a polypeptide-encoding nucleic acid sequence. The initiator codon encodes for the amino acid methionine, the so-called "start" codon. The initiator codon is typically an ATG, but may also be any functional start codon such as GTG. It is well known in the art that uracil, U, replaces the deoxynucleotide thymine, T, in RNA.

The term "consensus translational initiator sequence" is defined herein as the ten nucleotides immediately upstream of the initiator codon of the open reading frame of a polypeptide-encoding nucleic acid sequence having the following sequence:

5'-NYCNNHCACC-3' wherein N=A, G, C, or T; H=C or T; and H=A, C, or T. (SEQ ID NO. 1)

The present invention also relates to such isolated consensus translational initiator sequences. In a preferred embodiment, the consensus translational initiator sequence has the nucleic acid sequence 5'-GTCCTTCACC-3' (SEQ ID NO. 2), or a subsequence thereof that has the same biological activity as the consensus translational initiator sequence of SEQ ID NO. 2. In another preferred embodiment, the consensus translational initiator sequence has the nucleic acid sequence 5'-GTCCTCCACC-3' (SEQ ID NO. 3), or a subsequence thereof that has the same biological activity as the consensus translational initiator sequence of SEQ ID NO. 3. In another preferred embodiment, the consensus translational initiator sequence has the nucleic acid sequence 5'-GTCCTACACC-3' (SEQ ID NO. 4), or a subsequence thereof that has the same biological activity as the consensus translational initiator sequence of SEQ ID NO. 4.

The term "operably linked" is defined herein as a configuration in which a control sequence, e.g., a consensus translational initiator sequence, is appropriately placed at a position relative to a coding sequence such that the control sequence directs the production of a polypeptide encoded by the coding sequence.

The term "coding sequence" is defined herein as a nucleic acid sequence that is transcribed into mRNA which is translated into a polypeptide when placed under the control of the appropriate control sequences. The boundaries of the coding sequence are generally determined by the start codon located at the beginning of the open reading frame of the 5' end of the mRNA and a stop codon located at the 3' end of the open reading frame of the mRNA. A coding sequence can include, but is not limited to, genomic DNA, cDNA, semisynthetic, synthetic, and recombinant nucleic acid sequences.

In the methods of the present invention, the consensus translational initiator sequence is foreign to the nucleic acid sequence encoding a polypeptide of interest, but the consensus translational initiator sequence or nucleic acid sequence may be native to the fungal host cell.

Polypeptide Encoding Nucleic Acid Sequences

The polypeptide encoded by the nucleic acid sequence may be native or heterologous to the fungal host cell of interest.

The term "polypeptide" is not meant herein to refer to a specific length of the encoded product and, therefore, encompasses peptides, oligopeptides, and proteins. The term "heterologous polypeptide" is defined herein as a polypeptide which is not native to the fungal cell, a native polypeptide in which modifications have been made to alter the native sequence, or a native polypeptide whose expression is quantitatively altered as a result of a manipulation of the fungal cell by recombinant DNA techniques. For example, a native polypeptide may be recombinantly produced by, e.g., placing a gene encoding the polypeptide under the control of a consensus translational initiator sequence of the present invention to enhance expression of the polypeptide, to expedite export of a native polypeptide of interest outside the cell by use of a signal sequence, and to increase the copy number of a gene encoding the polypeptide normally produced by the cell. The fungal cell may contain one or more copies of the nucleic acid sequence encoding the polypeptide.

Preferably, the polypeptide is a hormone or variant thereof, enzyme, receptor or portion thereof, antibody or portion thereof, or reporter. In a preferred embodiment, the polypeptide is secreted extracellularly. In a more preferred embodiment, the polypeptide is an oxidoreductase, transferase, hydrolase, lyase, isomerase, or ligase. In an even more preferred embodiment, the polypeptide is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, pectinolytic enzyme, peroxidase, phospholipase, phytase, polyphenoloxidase, proteolytic enzyme, ribonuclease, transglutaminase, or xylanase.

The nucleic acid sequence encoding a polypeptide of interest may be obtained from any prokaryotic, eukaryotic, or other source. For purposes of the present invention, the term "obtained from" as used herein in connection with a given source shall mean that the polypeptide is produced by the source or by a cell in which a gene from the source has been inserted.

The techniques used to isolate or clone a nucleic acid sequence encoding a polypeptide of interest are known in the art and include isolation from genomic DNA, preparation from cDNA, or a combination thereof. The cloning of the nucleic acid sequence from such genomic DNA can be effected, e.g., by using the well known polymerase chain reaction (PCR). See, for example, Innis et al., 1990, *PCR Protocols: A Guide to Methods and Application*, Academic Press, New York. The cloning procedures may involve excision and isolation of a desired nucleic acid fragment comprising the nucleic acid sequence encoding the polypeptide, insertion of the fragment into a vector molecule, and incorporation of the recombinant vector into the mutant fungal cell where multiple copies or clones of the nucleic acid sequence will be replicated. The nucleic acid sequence may be of genomic, cDNA, RNA, semisynthetic, synthetic origin, or any combinations thereof.

In the methods of the present invention, the polypeptide may also include a fused or hybrid polypeptide in which another polypeptide is fused at the N-terminus or the C-terminus of the polypeptide or fragment thereof. A fused polypeptide is produced by fusing a nucleic acid sequence (or a portion thereof) encoding one polypeptide to a nucleic acid sequence (or a portion thereof) encoding another polypeptide. Techniques for producing fusion polypeptides are known in the art, and include, ligating the coding sequences encoding the polypeptides so that they are in frame and expression of the fused polypeptide is under control of the same promoter(s) and terminator. The hybrid polypeptide may comprise a combination of partial or complete polypeptide sequences obtained from at least two different polypeptides wherein one or more may be heterologous to the mutant fungal cell.

Nucleic Acid Constructs

The present invention also relates nucleic acid constructs comprising a nucleic acid sequence encoding a polypeptide operably linked to a consensus translational initiator sequence of the present invention and one or more control sequences which direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains a coding sequence and all the control sequences required for expression of the coding sequence.

An isolated nucleic acid sequence encoding a polypeptide may be further manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

In the methods of the present invention, the nucleic acid sequence may comprise one or more native control sequences or one or more of the native control sequences may be replaced with one or more control sequences foreign to the nucleic acid sequence for improving expression of the coding sequence in a host cell.

The term "control sequences" is defined herein to include all components which are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, consensus translational initiator sequence of the present invention, signal peptide sequence, and transcription terminator. At a minimum, the control sequences include a consensus translational initiator sequence of the present invention, and transcriptional and translational stop signals. The control sequences may be provided with linkers for the purpose of introducing specific restriction sites facilitating ligation of the control sequences with the coding region of the nucleic acid sequence encoding a polypeptide.

The control sequence may be an appropriate promoter sequence, a nucleic acid sequence which is recognized by a host cell for expression of the nucleic acid sequence. The promoter sequence contains transcriptional control sequences which mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase, *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, *Yeast* 8: 423–488.

The control sequence may be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983–5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

The present invention also relates to nucleic acid constructs for altering the expression of a gene encoding a polypeptide which is endogenous to a host cell. The constructs may contain the minimal number of components necessary for altering expression of the endogenous gene. In one embodiment, the nucleic acid constructs preferably contain (a) a targeting sequence, (b) a consensus translational initiator sequence of the present invention, (c) an exon, and (d) a splice-donor site. Upon introduction of the nucleic acid construct into a cell, the construct inserts by homologous recombination into the cellular genome at the endogenous gene site. The targeting sequence directs the integration of elements (a)–(d) into the endogenous gene such that elements (b)–(d) are operably linked to the endogenous gene. In another embodiment, the nucleic acid constructs contain (a) a targeting sequence, (b) a consensus translational initiator sequence of the present invention, (c) an exon, (d) a splice-donor site, (e) an intron, and (f) a splice-acceptor site, wherein the targeting sequence directs the integration of elements (a)–(f) such that elements (b)–(f) are operably linked to the endogenous gene. However, the constructs may contain additional components such as a selectable marker.

In both embodiments, the introduction of these components results in production of a new transcription unit in which expression of the endogenous gene is altered. In essence, the new transcription unit is a fusion product of the sequences introduced by the targeting constructs and the endogenous gene. In one embodiment in which the endogenous gene is altered, the gene is activated. In this embodiment, homologous recombination is used to replace, disrupt, or disable the regulatory region normally associated with the endogenous gene of a parent cell through the insertion of a regulatory sequence which causes the gene to be expressed at higher levels than evident in the corresponding parent cell. The activated gene can be further amplified by the inclusion of an amplifiable selectable marker gene in the construct using methods well known in the art (see, for example, U.S. Pat. No. 5,641,670). In another embodiment in which the endogenous gene is altered, expression of the gene is reduced.

The targeting sequence can be within the endogenous gene, immediately adjacent to the gene, within an upstream gene, or upstream of and at a distance from the endogenous gene. One or more targeting sequences can be used. For example, a circular plasmid or DNA fragment preferably employs a single targeting sequence, while a linear plasmid or DNA fragment preferably employs two targeting sequences.

The constructs further contain one or more exons of the endogenous gene. An exon is defined as a DNA sequence which is copied into RNA and is present in a mature mRNA molecule such that the exon sequence is in-frame with the coding region of the endogenous gene. The exons can, optionally, contain DNA which encodes one or more amino acids and/or partially encodes an amino acid. Alternatively, the exon contains DNA which corresponds to a 5' non-encoding region. Where the exogenous exon or exons encode one or more amino acids and/or a portion of an amino acid, the nucleic acid construct is designed such that, upon transcription and splicing, the reading frame is in-frame with the coding region of the endogenous gene so that the appropriate reading frame of the portion of the mRNA derived from the second exon is unchanged.

The splice-donor site of the constructs directs the splicing of one exon to another exon. Typically, the first exon lies 5' of the second exon, and the splice-donor site overlapping and flanking the first exon on its 3' side recognizes a splice-acceptor site flanking the second exon on the 5' side of the second exon. A splice-acceptor site, like a splice-donor site, is a sequence which directs the splicing of one exon to another exon. Acting in conjunction with a splice-donor site, the splicing apparatus uses a splice-acceptor site to effect the removal of an intron.

The present invention further relates to methods for producing a polypeptide comprising (a) cultivating a homologously recombinant cell, having incorporated therein a new transcription unit comprising a consensus translational initiator sequence of the present invention, an exon, and/or a splice donor site operably linked to a second exon of an endogenous nucleic acid sequence encoding the polypeptide, under conditions conducive for production of the polypeptide; and (b) recovering the polypeptide. The methods are based on the use of gene activation technology, for example, as described in U.S. Pat. No. 5,641,670.

Expression Vectors

The present invention also relates to recombinant expression vectors comprising a consensus translational initiator sequence of the present invention, a nucleic acid sequence encoding a polypeptide, and transcriptional and translational stop signals. The various nucleic acid and control sequences described above may be joined together to produce a recombinant expression vector which may include one or more convenient restriction sites to allow for insertion or substitution of the promoter and/or nucleic acid sequence encoding the polypeptide at such sites. Alternatively, the nucleic acid sequence may be expressed by inserting the nucleic acid sequence or a nucleic acid construct comprising the consensus translational initiator sequence and/or sequence into an appropriate vector for expression. In creating the expression vector, the coding sequence is located in the vector so that the coding sequence is operably linked with a consensus translational initiator sequence of the present invention and one or more appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an Aspergillus cell are the amdS and pyrG genes of *Aspergillus nidulans* or *Aspergillus oryzae* and the bar gene of *Streptomyces hygroscopicus*. T he vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes its functioning temperature-sensitive in the host cell (see, e.g., Ehrlich, 1978, *Proceedings of the National Academy of Sciences USA* 75: 1433).

More than one copy of a nucleic acid sequence encoding a polypeptide may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a consensus translational initiator sequence of the present invention operably linked to a nucleic acid sequence encoding a polypeptide, which are advantageously used in the recombinant production of the polypeptides. A vector comprising a consensus translational initiator sequence of the present invention operably linked to a nucleic acid sequence encoding a polypeptide is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any fungal cell useful in the methods of the present invention. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a preferred embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and *Activities of Yeast* (Skinner, F. A., Passmore, S. M., and Davenport, R. R., eds, *Soc. App. Bacteriol. Symposium Series* No. 9, 1980).

In a more preferred embodiment, the yeast host cell is a Candida, Hansenula, Kluyveromyces, Pichia, Saccharomyces, Schizosaccharomyces, or Yarrowia cell.

In a most preferred embodiment, the yeast host cell is a *Saccharomyces carlsbergensis, Saccharomyces cerevisiae, Saccharomyces diastaticus, Saccharomyces douglasii, Saccharomyces kluyveri, Saccharomyces norbensis* or *Saccharomyces oviformis* cell. In another most preferred embodiment, the yeast host cell is a *Kluyveromyces lactis* cell. In another preferred embodiment, the yeast host cell is a *Yarrowia lipolytica* cell.

In another preferred embodiment, the fungal host cell is a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In a more preferred embodiment, the filamentous fungal host cell is a cell of a species of, but not limited to, Acremonium, Aspergillus, Fusarium, Humicola, Mucor, Myceliophthora, Neurospora, Penicillium, Thielavia, Tolypocladium, or Trichoderma.

In a most preferred embodiment, the filamentous fungal host cell is an *Aspergillus awamori, Aspergillus foetidus, Aspergillus japonicus, Aspergillus nidulans, Aspergillus niger* or *Aspergillus oryzae* cell. In another most preferred embodiment, the filamentous fugal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred embodiment, the filamentous fungal host cell is a *Humicola insolens, Humicola lanuginosa, Mucor miehei, Myceliophthora thermophila, Neurospora crassa, Penicillium purpurogenum, Thielavia terrestris, Trichoderma harzianum, Trichoderma koningii, Trichoderma longibrachiatum, Trichoderma reesei,* or *Trichoderma viride* cell.

In an even most preferred embodiment, the *Fusarium venenatum* cell is *Fusarium venenatum* A3/5, which was originally deposited as *Fusarium graminearum* ATCC 20334 and recently reclassified as *Fusarium venenatum* by Yoder and Christianson, 1998, *Fungal Genetics and Biology* 23: 62–80 and O'Donnell et al., 1998, *Fungal Genetics and Biology* 23: 57–67; as well as taxonomic equivalents of *Fusarium venenatum* regardless of the species name by which they are currently known. In another preferred embodiment, the *Fusarium venenatum* cell is a morphological mutant of *Fusarium venenatum* A3/5 or *Fusarium venenatum* ATCC 20334, as disclosed in WO 97/26330.

Fungal cells may be transformed by a process involving protoplast formation, transformation of the protoplasts, and regeneration of the cell wall in a manner known per se. Suitable procedures for transformation of Aspergillus host cells are described in EP 238 023 and Yelton et al., 1984, *Proceedings of the National Academy of Sciences USA* 81: 1470–1474. Suitable methods for transforming Fusarium species are described by Malardier et al., 1989, *Gene* 78: 147–156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182–187, Academic Press, Inc., New York; Ito et al., 1983, *Journal of Bacteriology* 153: 163; and Hinnen et al., 1978, *Proceedings of the National Academy of Sciences USA* 75: 1920.

The present invention is further described by the following examples which should not be construed as limiting the scope of the invention.

EXAMPLES

Chemicals used as buffers and substrates were commercial products of at least reagent grade.

Media and Solutions

MY25 medium at pH 6.5 was composed per liter of 25 g of maltose, 2.0 g of $MgSO_4 \cdot 7H_2O$, 10 g of $KH_2PO_4$, 2.0 g of citric acid, 10 g of yeast extract, 2.0 g f $K_2SO_4$, 2.0 g of urea, 1.0 ml of $CaCl_2 \cdot 2H_2O$ (100 g/l stock solution), and 0.5 ml of trace metals solution. MY25 microtiter medium was diluted 1:100 with 490 ml glass distilled water and 500 ml 2×MY Salts. Cultures were grown at 34° C.

2×MY Salts pH 6.5 solution was composed per liter of 4 g of $MgSO_4 \cdot 7H_2O$, 4 g of $K_2SO_4$, 20 g of $KH_2PO_4$, 4 g of citric acid, 1 ml of trace metals solution, and 2 ml of $CaCl_2 \cdot 2H_2O$ (100 g/l stock solution).

Minimal medium transformation plates were composed per liter of 6 g of $NaNO_3$, 0.52 g of KCl, 1.52 g of $KH_2PO_4$, 1 ml of trace metals solution, 10 g of glucose, 500 mg of $MgSO_4 \cdot 7H_2O$, 342.3 g of sucrose, and 20 g of Noble agar (pH 6.5). Minimal medium transfer plates (pH 6.5) were composed per liter of 6 g of $NaNO_3$, 0.52 g of KCl, 1.52 g of $KH_2PO_4$, 1 of trace elements, 1 g of glucose, 500 mg of $MgSO_4 \cdot 7H_2O$, and 20 g Noble agar.

Acetate Medium with fluoroacetamide was composed per liter of 12.77 g of sodium acetate, 2 g of sodium chloride, 500 mg of $MgSO_4 \cdot 7H_2O$, 3 g of $KH_2PO_4$, 300 mg of urea, trace ferrous sulfate and zinc sulfate, 342.3 g of sucrose, 2 g of fluoroacetamide and 12 g of Noble agar at pH 6.1.

Minimal Medium was composed per liter of 6 g of $NaNO_3$, 0.52 g of KCl, 1.52 g of $KH_2PO_4$, 1 ml trace metals, 10 g of glucose, 500 mg of $MgSO_4 \cdot 7H_2O$, 342.3 g of sucrose, and 20 g of Noble agar at pH 6.5. Transfer plates were the same as above, but omitting the sucrose.

The trace metals solution (1000×) was composed per liter of 22 g of $ZnSO_4 \cdot 7H_2O$, 11 g of $H_3BO_3$, 5 g of $MnCl_2 \cdot 4H_2O$, 5 g of $FeSO_4 \cdot 7H_2O$, 1.6 g of $CoCl_2 \cdot 5H_2O$, 11 g $(NH_4)_6Mo_7O_{24}$, and 50 g of $Na_4EDTA$.

Chlorate plate was composed of Minimal Medium supplemented 470 mM chlorate and 10 mM glutamate as sole nitrogen source.

COVE plates were composed per liter of 343.3 g of sucrose, 20 ml of COVE salts solution, 10 ml of 1 M acetamide, 10 ml of 3 M CsCl, and 25 g of Nobel agar. The COVE salts (50×) solution was composed per liter of 26 g of KCl, 26 g of $MgSO_4 \cdot 7H_2O$, 76 g of $KH_2PO_4$, and 50 ml of COVE trace metals solution. COVE trace metals solution was composed per liter of 0.04 g of $NaB_4O_7 \cdot 10H_2O$, 0.040 g of $CuSO_4 \cdot 5H_2O$, 0.70 g of $FeSO_4 \cdot H_2O$, 0.80 g of $Na_2MoO_2 \cdot 2H_2O$, and 10 g of $ZnSO_4$.

COVE overlay was composed per liter of 0.52 g of KCl, 0.52 g of $MgSO_4 \cdot 7H_2O$, 1.52 g of $KH_2PO_4$, 1 ml of trace metals, 0.8 M sucrose, and 1% low melt agar was used to dispense them onto the transformation plates.

YEG medium was composed per liter of 5 g yeast extract and 20 g dextrose.

Example 1

Construction of pBANe8 pBANe8 was constructed as described below to contain the TAKA/NA2-tpi leader hybrid promoter, the lipase gene from *Humicola lanuginosa* bordered by a PacI and SwaI site, the AMG terminator, and the full-length *Aspergillus nidulans* amdS gene as a selectable marker.

PCR was employed to insert NsiI sites flanking the full-length amdS gene of pToC90 (Christensen et al., 1988, *Biotechnology* 6: 1419–1422) using primers 1 and 2 below and to insert an EcoRI site at the 5' end and a SwaI site at the 3' end of the NA2-tpi leader hybrid promoter of pJaL292 (FIG. 1) using primers 3 and 4 below. The primers were synthesized with an Applied Biosystems Model 394 DNA/RNA Synthesizer (Applied Biosystems, Inc., Foster City, Calif.) according to the manufacturer's instructions.

Primer 1: 5'-ATGCATCTGGAAACGCAACCCTGA-3' (SEQ ID NO. 5)

Primer 2: 5'-ATGCATTCTACGCCAGGACCGAGC-3' (SEQ ID NO. 6)

Primer 3: 5'-TGGTGTACAGGGGCATAAAAT-3' (SEQ ID NO. 7)

Primer 4: 5'-ATTTAAATCCAGTTGTGTATATAGAGGATTG TGG-3' (SEQ ID NO. 8)

Amplification reactions (100 µl) were prepared using approximately 0.2 µg of either pToC90 or pJaL292 as the template. Each reaction contained the following components: 0.2 µg of plasmid DNA, 48.4 pmol of the forward primer, 48.4 pmol of the reverse primer, 1 mM each of dATP, dCTP, dGTP, and dTTP, 1×Taq DNA polymerase buffer, and 2.5 U of Taq DNA polymerase (Perkin-Elmer Corp., Branchburg, N.J.). The reactions were incubated in an Ericomp TwinBlock™ System (Ericomp, Inc., San Diego, Calif.) programmed as follows: One cycle at 95° C. for 5 minutes followed by 30 cycles each at 95° C. for 1 minute, 55° C. for 1 minute 72° C. for 2 minutes.

The PCR products were electrophoresed on a 1% agarose gel to confirm the presence of a 2.7 kb amdS fragment and a 0.6 kb NA2-tpi fragment.

Figure 2:
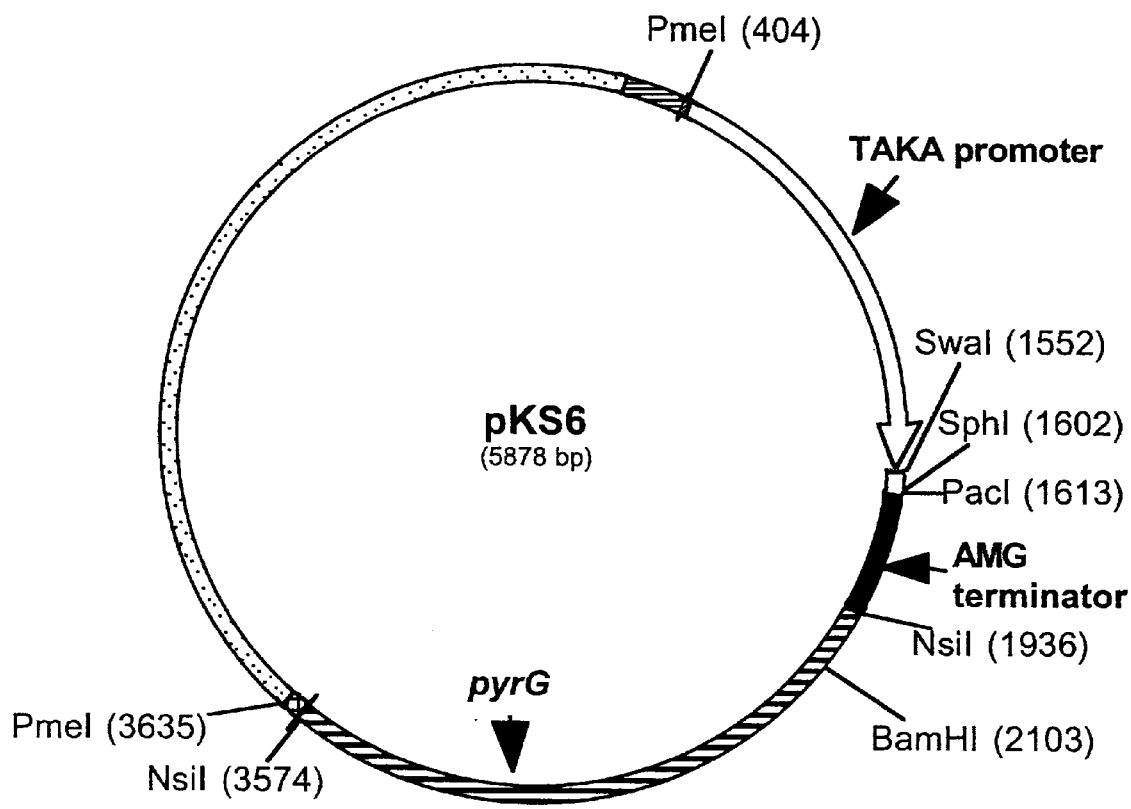
FIG. 2 shows a restriction map of pKS6.
Figure 3:
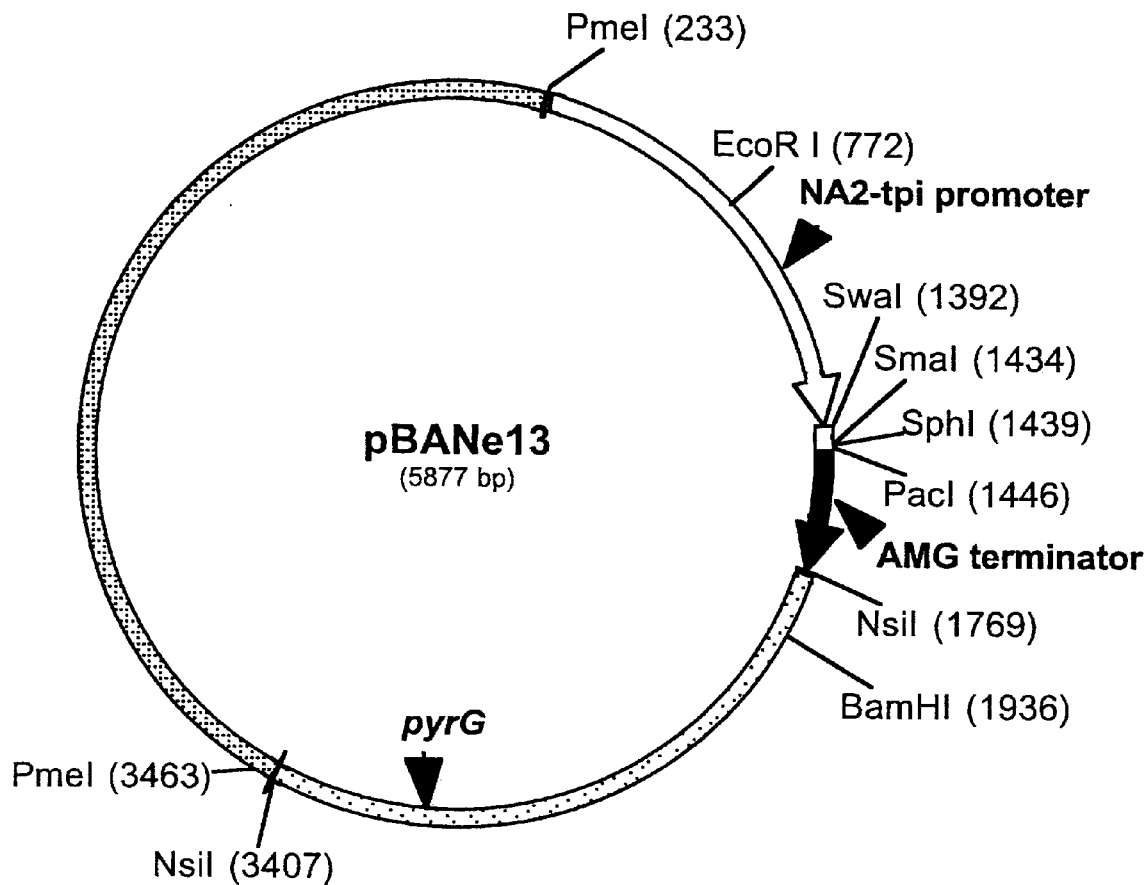
FIG. 3 shows a restriction map of pBANe13.
Figure 4:
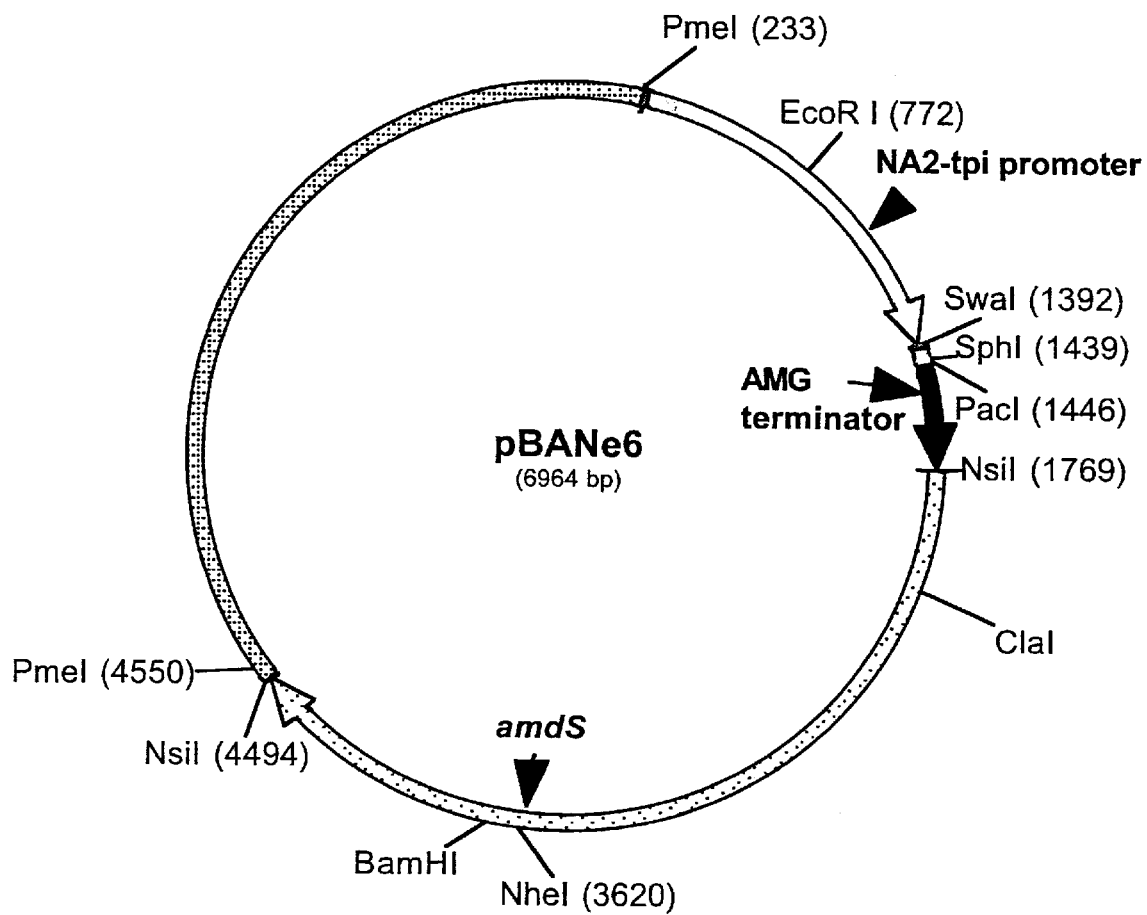
FIG. 4 shows a restriction map of pBANe6.

The PCR products were subsequently subcloned into pCRII using a TA Cloning Kit (Invitrogen, San Diego, Calif.) according to the manufacturer's instructions. The transformants were then screened by extracting plasmid DNA from the transformants using a QIAwell-8 Plasmid Kit (Qiagen, Inc., Chatsworth, Calif.) according to the manufacturer's instructions, and restriction digesting the plasmid DNA with either NsiI or EcoRI/SwaI followed by agarose electrophoresis to confirm the presence of the correct size fragments, 2.7 kb and 0.6 kb, respectively, for the NsiI amdS fragment and SwaI/EcoRI NA2-tpi fragment. In order to confirm the PCR products, the products were sequenced with an Applied Biosystems Model 373A Automated DNA Sequencer (Applied Biosystems, Inc., Foster City, Calif.) on both strands using the primer walking technique with dye-terminator chemistry (Giesecke et al., 1992, *Journal of Virol. Methods* 38: 47–60) using the M13 reverse (–48) and M13 forward (–20) primers (New England Biolabs, Beverly, Mass.) and primers unique to the DNA being sequenced. The plasmids from the correct transformants were then digested with the restriction enzymes for which the plasmids were designed, separated on a 1% agarose gel, and purified using a FMC SpinBind Kit (FMC, Rockland, Me.) according to the manufacturer's instructions.

pKS6 (FIG. 2), which contains the TAKA amylase promoter, a polylinker, the AMG terminator, and the *Aspergillus nidulans* pyrG gene, was digested with EcoRI and SwaI to remove a portion of the TAKA amylase promoter. This region was replaced with the NA2-tpi PCR product to produce pBANe13 (FIG. 3).

pBANe13 was digested with NsiI to remove the *Aspergillus nidulans* pyrG gene. This region was then replaced with the full length amdS gene PCR product described above to produce pBANe6 (FIG. 4).

Figure 5:
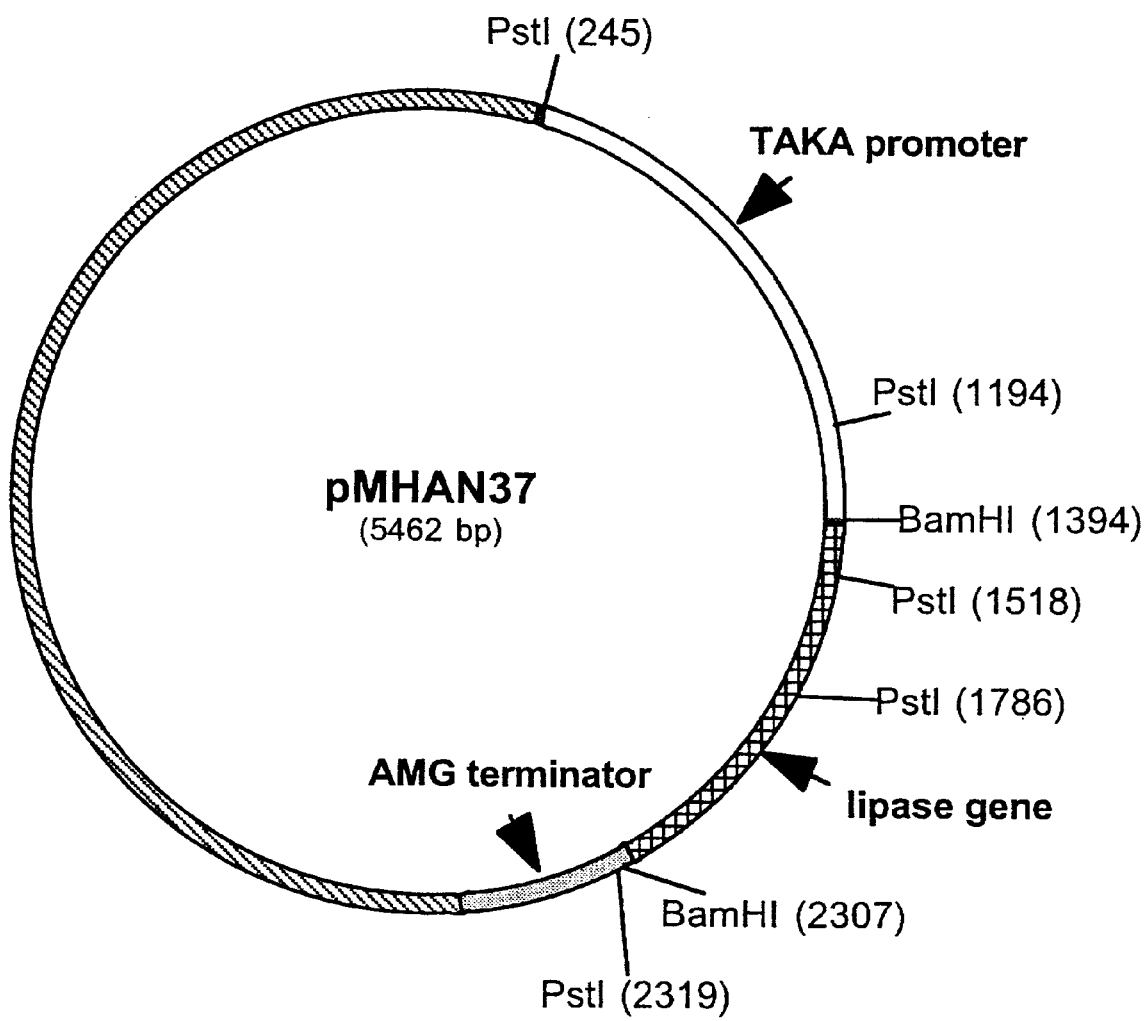
FIG. 5 shows a restriction map of pMHan37.

PCR was used to insert SwaI and PacI flanking sites on the full-length *Humicola lanuginosa* lipase gene of pMHan37 (FIG. 5) using primers 5 and 6 below. Primers 5 and 6 were synthesized as described above.

Primer 5:
5'-ATTTAAATGATGAGGAGCTCCCTTGTGCTG-3' (SEQ ID NO. 9)

Primer 6:
5'-TTAATTAACTAGAGTCGACCCAGCCGCGC-3' (SEQ ID NO. 10)

The amplification reaction (100 µl) contained the following components: 100 ng of pMHan37, 48.4 pmol of primer 5, 48.4 pmol of primer 6, 1 mM each of dATP, dCTP, dGTP, and dTTP, 1×Taq DNA polymerase buffer, and 2.5 U of Taq DNA polymerase. The reaction was incubated in an Ericomp TwinBlock™ System programmed as follows: One cycle at 95° C. for 5 minutes followed by 30 cycles each at 95° C. for 1 minute, 55° C. for 1 minute, and 72° C. for 2 minutes. Two µl of the reaction was electrophoresed on a 1% agarose gel to confirm the amplification of the lipase gene product of approximately 900 bp.

The PCR amplified lipase gene product was then subcloned into pCRII using a TA Cloning Kit. The transformants were screened by extracting plasmid DNA from the transformants using a QIAwell-8 Plasmid Kit, restriction digesting the plasmid DNA with SwaI/PacI, and sequencing the DNA according to the method described above to confirm the PCR product.

Figure 6:
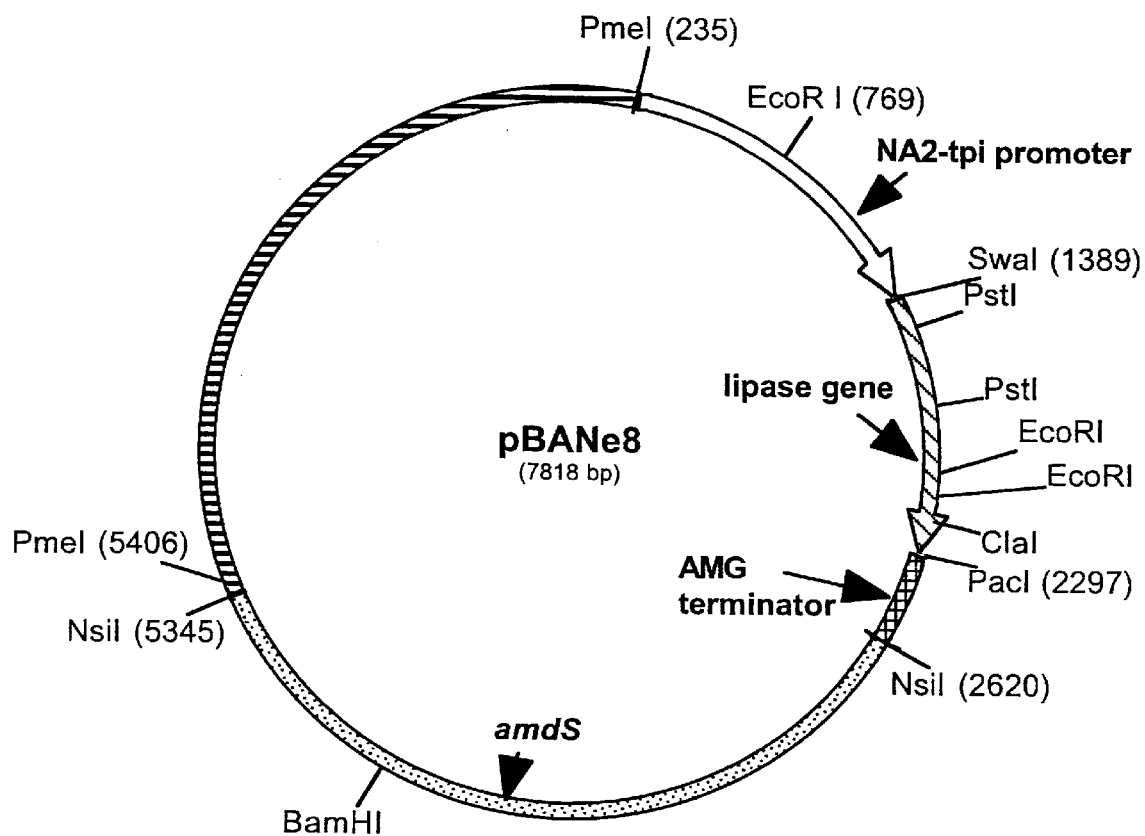
FIG. 6 shows a restriction map of pBANe8.

The lipase gene was excised from the pCRII plasmid by digesting with SwaI and PacI and subsequently subcloned into SwaI/PacI digested pBANe6 to produce pBANe8 (FIG. 6).

Example 2

Construction of pBANe15

Plasmid pBANe15 was constructed to contain the *Aspergillus nidulans* amdS gene and a polylinker site between the *Aspergillus oryzae* alpha-amylase promoter and *Aspergillus niger* glucoamylase terminator.

PCR was used to insert NsiI sites at both ends of the full length amdS gene using primers 7 and 8 described below which were synthesized using an Applied Biosystems Model 394 DNA/RNA Synthesizer, according to the manufacturer's instructions.

Primer 7: 5'-ATGCATCTGGAAACGCAACCCTGA-3' (SEQ ID NO. 11)

Primer 8: 5'-ATGCATTCTACGCCAGGACCGAGC-3' (SEQ ID NO. 12)

Amplification reactions (100 µl) were prepared using approximately 0.2 µg of pToC90 (Christensen et al., 1988, *Biotechnology* 6:1419–1422) as template. The reaction contained the following components: 0.2 µg of pToC90, 48.4 pmol primer 7, 48.4 pmol primer 8, 1 mM each dNTP, 1×Taq polymerase buffer, and 2.5 U Taq polymerase (Perkin-Elmer Corp., Branchburg, N.J.). The reactions are incubated in an Ericomp TwinBlock™ System programmed as follows: One cycle at 95° C. for 5 minutes followed by 30 cycles each at 95° C. for 1 minute, 55° C. for 1 minute and 72° C. for 2 minutes.

Figure 7:
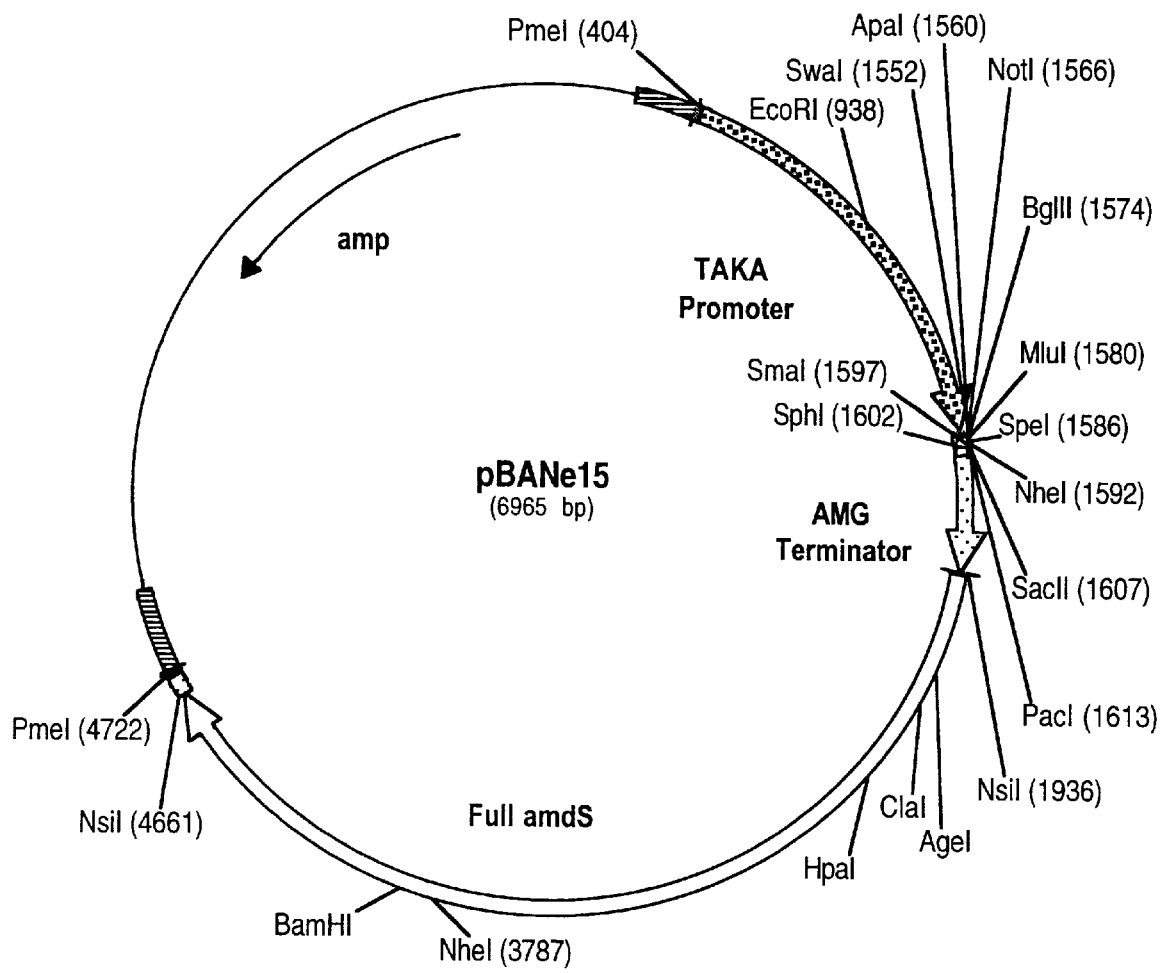
FIG. 7 shows a restriction map of pBANe15.

The PCR products were subsequently subcloned into pCRII using the TA Cloning Kit according to the manufacturer's instructions. The transformants were then screened by extracting plasmid DNA from the transfornants using a QIAwell-8 Plasmid Kit (Qiagen, Inc., Chatsworth, Calif.) according to the manufacturer's instructions, restriction digesting the plasmid DNA with NsiI to confirm the presence of the correct size fragment, and sequencing the DNA according to the method described in Example 1 to confirm the PCR product. The plasmids from the correct transformants were then digested with NsiI, separated on a 1% agarose gel, and purified using a FMC SpinBind Kit according to the manufacturer's instructions.

pKS6 was digested with NsiI to remove the *Aspergillus nidulans* pyrG gene, which was then replaced with the full length amdS gene NsiI fragment described above to produce pBANe15 (FIG. 7).

Example 3

Construction of pDBEL1 and its Variants

Figure 8:
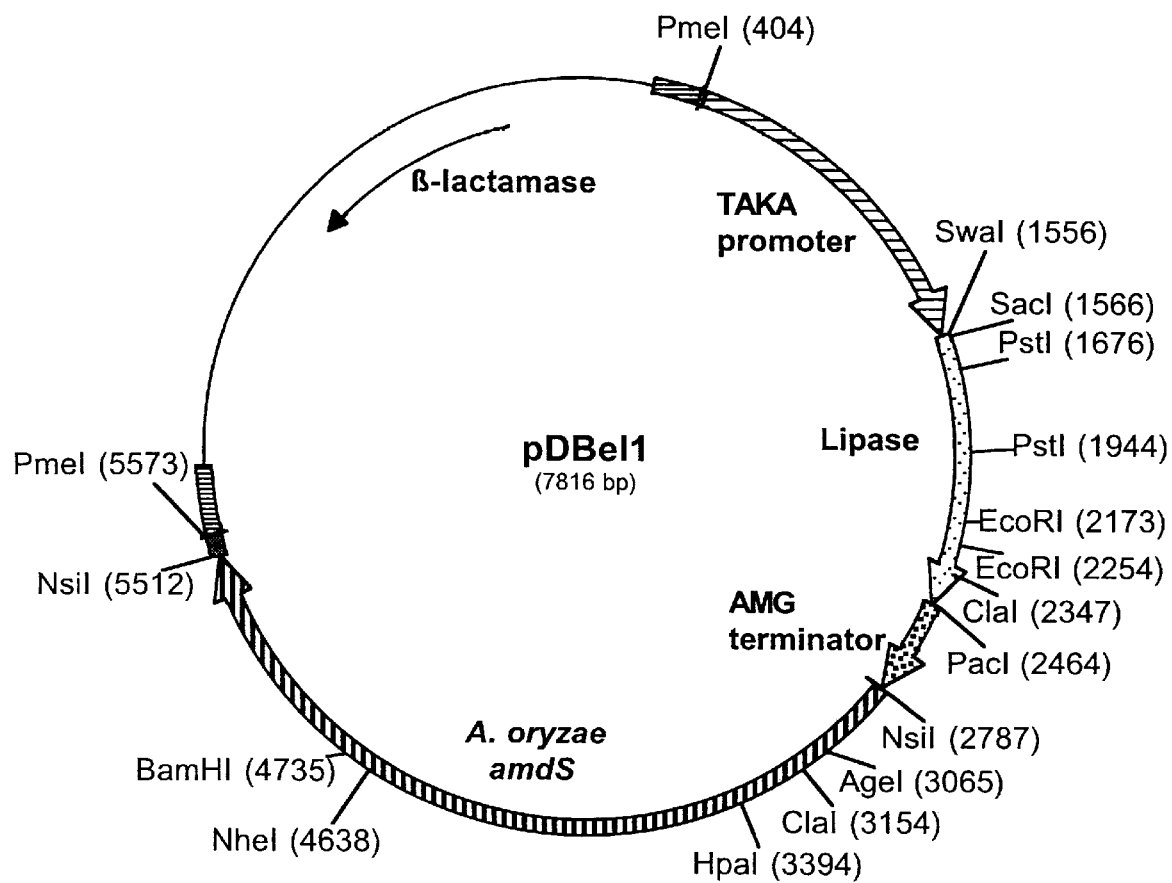
FIG. 8 shows a restriction map of pDBEL1.

Plasmids pBANe8 and pBANe15 were each digested with PacI and SwaI. After digestion, 25 µl of each reaction was electrophoresed on a 1% agarose gel using 40 mM Tris-acetate-1 mM disodium EDTA (TAE) buffer. The appropriate size fragments (6904 bp pBANe15 fragment and 908 bp lipase fragment) were excised from the gel and purified using a Qiagen Gel Extraction Kit (Qiagen, Inc., Chatsworth, Calif.) following the manufacturer's instructions. These fragments were ligated together with T4 DNA ligase to produce pDBEL1 (FIG. 8), which contained the *Aspergillus nidulans* amdS gene, the *Aspergillus oryzae* alpha-amylase promoter and *Aspergillus niger* glucoamylase terminator from pBANe15, and the *Humicola lanuginosa* lipase gene from pBANe8. The nucleotide sequence of the translational initiator region upstream of the *Humicola lanuginosa* lipase gene in pDBEL1 was determined to be CATTTAAATGATG (SEQ ID NO. 13) with the minus 3 position containing an A nucleotide.

The minus 3 position upstream of the *Humicola lanuginosa* lipase gene was changed using a Stratagene QuikChange™ Site-Directed Mutagenesis Kit (Stratagene Cloning Systems, La Jolla, Calif.) following the manufacturer's instructions and using the primers listed below. Three variants of pDBEL1 were produced each differing only by the nucleotide at the minus 3 position.

Primer 9:
5'-CCACAGAAGGCATTTAATTGATGAGGAGCT CCCTTG-3' (SEQ ID NO. 14)

Primer 10:
5'-CAAGGGAGCTCCTCATCAATTAAATGCCTT CTGTGG-3' (SEQ ID NO. 15)

Primer 11:
5'-CCACAGAAGGCATTTAACTGATGAGGAGC TCCCTTG-3' (SEQ ID NO. 16)

Primer 12:
5'-CAAGGGAGCTCCTCATCAGTTAAATGCCTT CTGTGG-3' (SEQ ID NO. 17)

Primer 13:
5'-CCACAGAAGGCATTTAAGTGATGAGGAGC TCCCTTG-3' (SEQ ID NO. 18)

Primer 14:
5'-CAAGGGAGCTCCTCATCACTTAAATGCCTT CTGTGG-3' (SEQ ID NO. 19)

Primers 9 and 10 were used to produce pDBEL1T, primers 11 and 12 to produce pDBEL1C, and primers 13 and 14 to produce pDBEL1G. Each reaction contained the following components: 100 ng of pDBEL1, 50 pmol of the forward primer, 50 pmol of the reverse primer, 200 µM each of dATP, dCTP, dGTP, and dTTP, 1×Taq DNA polymerase buffer (Invitrogen, San Diego, Calif.), and 2.5 Units of Taq DNA polymerase (Perkin-Elmer Corp., Branchburg, N.J.).

The reactions were incubated in a Perkin-Elmer Model 9600 Thermocycler programmed as follows: One cycle at 95° C. for 30 seconds followed by 12 cycles each at 95° C. for 30 seconds, 55° C. for 1 minute, and 68° C. for 14 minutes. PCR reactions treated with 10 units of Dpn I to digest the non-mutated parental DNA. The reactions were then used to transform *E. coli* XL1-Blue supercompetent cells following the Stratagene QuikChange™ Site-Directed Mutagenesis kit protocol.

The nucleotide sequence of the pDBEL1 variants (PDBEL1T, pDBEL1C, pDBEL1G) was determined using Taq polymerase cycle-sequencing with fluorescent labeled nucleotides. The sequencing reactions were electrophoresed on an Applied Biosystems Automatic DNA Sequencer Model 377, version 3.0. The sequencing primers used are listed below.

Sequencing primer 971308:
5'-AGAGTGACTAGGGGCGGAAAT-3' (SEQ ID NO. 20)

Sequencing primer 971309:
5'-CCGGTGACATCGCCCACTCCA-3' (SEQ ID NO. 21)

The nucleotide sequences of the pDBEL1 variants were as follows:

```
pDBBL1T    CATTTAATTGATG    (SEQ ID NO.22)
pDBBL1C    CATTTAACTGATG    (SEQ ID NO.23)
pDBEL1G    CATTTAAGTGATG    (SEQ ID NO.24)
```

Example 4

Construction of *Aspergillus oryzae* BANe3

*Aspergillus oryzae* HowB711 was grown in 25 ml of 0.5% yeast extract-2% glucose (YEG) medium for 24 hours at 37° C. and 250 rpm. Mycelia were then collected by filtration through Miracloth (Calbiochem, La Jolla, Calif.) and washed three times with distilled water. Excess water was drained from the mycelia preparation which was subsequently frozen in liquid nitrogen. The frozen mycelia preparation was ground to a fine powder with a mortar and pestle, and the powder was added to a disposable plastic centrifuge tube containing 20 ml of 10 mM Tris-1 mM EDTA (TE) buffer and 5 ml of 20% w/v sodium dodecylsulfate (SDS). The mixture was gently inverted several times to ensure mixing, and extracted twice with an equal volume of phenol:chloroform:isoamyl alcohol (25:24:1 v/v/v). Sodium acetate (3 M solution) was added to the extracted sample to a final concentration of 0.3 M followed by 2.5 volumes of ice cold ethanol to precipitate the DNA. The tube was centrifuged at 15,000×g for 30 minutes to pellet the DNA. The DNA pellet was allowed to air-dry for 30 minutes before resuspension in 0.5 ml of TE buffer. DNase-free ribonuclease A was added to the resuspended DNA pellet to a concentration of 100 μg per ml and the mixture was then incubated at 37° C. for 30 minutes. Proteinase K (200 μg/ml) was added and the tube was incubated an additional one hour at 37° C. Finally, the sample was extracted twice with phenol:chloroform:isoamyl alcohol and the DNA precipitated with ethanol. The precipitated DNA was washed with 70% ethanol, dried under vacuum, resuspended in TE buffer, and stored at 4° C.

The amdS gene was PCR amplified from the *Aspergillus oryzae* HowB711 genomic DNA isolated as described above using primers 15 and 16 shown below. The primers are based on the *Aspergillus oryzae* amdS gene sequence reported by Gomi et al. (1991, *Gene* 108: 91–98). The reaction contained the following components: 200 ng of genomic DNA, 50 pmol of the forward primer, 50 pmol of the reverse primer, 200 μM each of dATP, dCTP, dGTP, and dTTP, 1×Taq DNA polymerase buffer (Invitrogen, San Diego, Calif.), and 2.5 Units of Taq DNA polymerase (Perkin-Elmer Corp., Branchburg, N.J.). The reactions were incubated in a Ericomp TwinBlock™ System programmed as follows: One cycle at 95° C. for 5 minutes followed by 30 cycles each at 95° C. for 1 minute, 55° C. for 1 minute, and 72° C. for 1.5 minutes.

Primer 15 (95–589)
5'-GGTCCAGACAACTCCCAGAAC-3' (SEQ ID NO. 25)

Primer 16 (95–590)
5'-CGAGGCGTGCGTAGTAGGTCT-3' (SEQ ID NO. 26)

Ten μl of the reaction was electrophoresed on an 1% agarose gel using TAE buffer which yielded a product of 2660 bp. The 2660 bp fragment was subcloned into pCRII and then transformed into One Shot Cells (*E. coli* TOP10 competent cells) using the TA Cloning Kit according to the manufacturer's protocol. The nucleotide sequence was determined to confirm the PCR product was amdS using Taq DNA polymerase cycle-sequencing with fluorescent labeled nucleotides of M13 reverse (–48) and M13 forward (–20) primers using an Applied Biosystems Automatic DNA Sequencer (Model 373A, version 1.2.0).

pUC4L was constructed by digesting pUC4K (Pharmacia, Uppsala, Sweden) with PstI and treating the digested plasmid with calf alkaline phosphates. The digested plasmid was electrophoresed on a 1% agarose gel using TAE buffer and a band of 3.9 kb was excised from the gel. The excised DNA was purified using a Prep-a-Gene Kit (BioRad, Hercules, Calif.). The following self-complimentary oligonucleotide was used to create a linker in pUC4k-PstI:

5'-GCCCGGGATCGATGCATCTAGATATCTAGATG
CATCGATCCCGGGCTGCA-3' (SEQ ID NO. 27)

Figure 9:
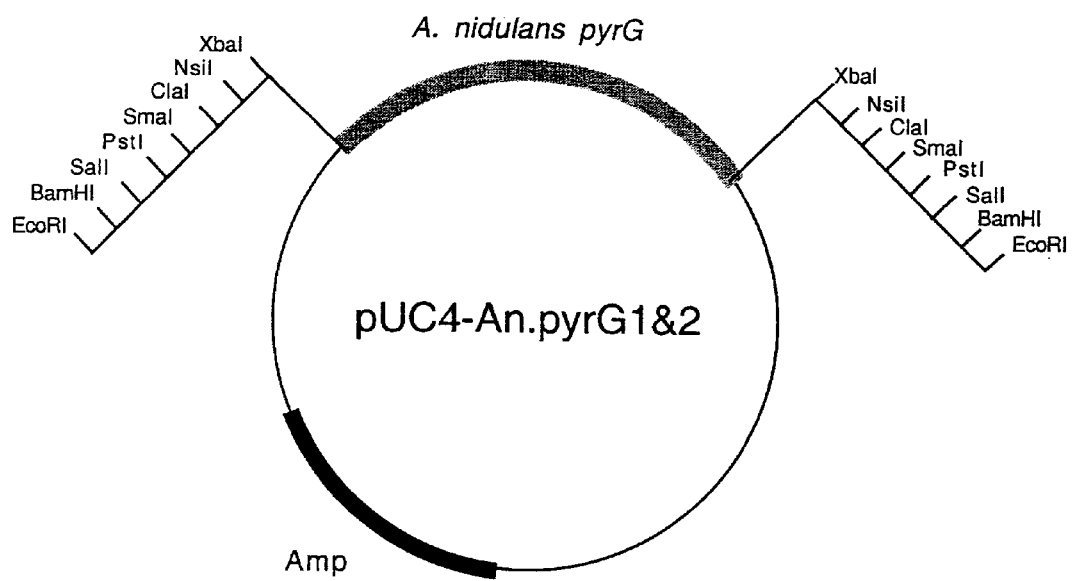
FIG. 9 shows a restriction map of pUC4-AN.pyrG1 & 2.

The oligonucleotide was treated with T4 kinase in the presence of 1.0 mM ATP under standard conditions, heated at 68° C. for 30 minutes, and allowed to anneal by slow cooling to room temperature for 30 minutes. The annealed primer and digested pUC4K were ligated together and used to transform *E. coli* DH5α. Colonies were screened by isolating the DNA and restriction digesting the DNA with XbaI and also StuI plus ScaI. pUC4L was then isolated using a Wizard Midiprep Kit (Promega, Madison, Wis.).

pUC4-AN.pyrG1&2 (FIG. 9) was constructed by digesting pUC4L with EcoRV and treating the digested plasmid with calf alkaline phosphatase. The digested and phosphatased pUC4L was electrophoresed using a 1% agarose gel with TAE buffer to isolate an approximately 3.9 kb fragment. The 3.9 kb EcoRV fragment was excised and gel purified using BioRad Prep-A-Gene Kit. The purified EcoRV fragment was ligated with an approximately 1.6 kb fragment containing the *Aspergillus nidulans* pyrG gene from pPYRG1 (Fungal Genetics Stock Center, Kansas City, Kans.). pPYRG1 was digested with ScaI and NdeI and then treated with Klenow fragment in the presence of dNTPs to fill-in the ends. The fragment was then electrophoresed on a 1% agarose gel using TAE buffer, and a band containing the 1.6 kb *Aspergillus nidulans* pyrG fragment was excised. The pyrG fragment was purified using a BioRad Prep-A-Gene Kit.

The ligation of pUC4L and the pyrG fragment was used to transform *E. coli* DH5α. The transformants were screened by hybridization using the *Aspergillus oryzae* pyrG gene as a probe obtained as a 1.7 kb fragment from pJeRS4 (U.S. Pat. No. 5,861,280). Four positive colonies were identified and further analyzed by restriction digest with XbaI to confirm the presence of the Aspergillus nidulans pyrg1 gene.

Figure 10:
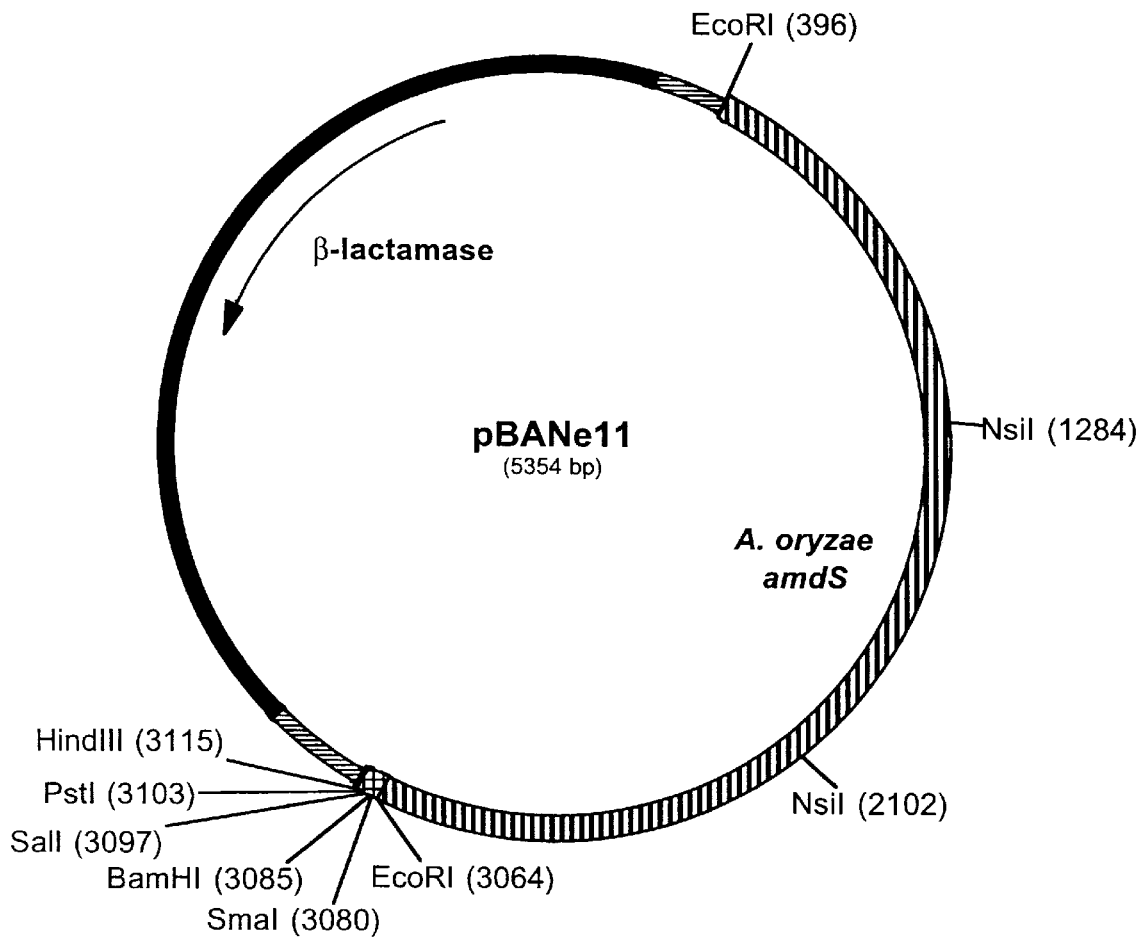
FIG. 10 shows a restriction map of pBANe11.
Figure 11:
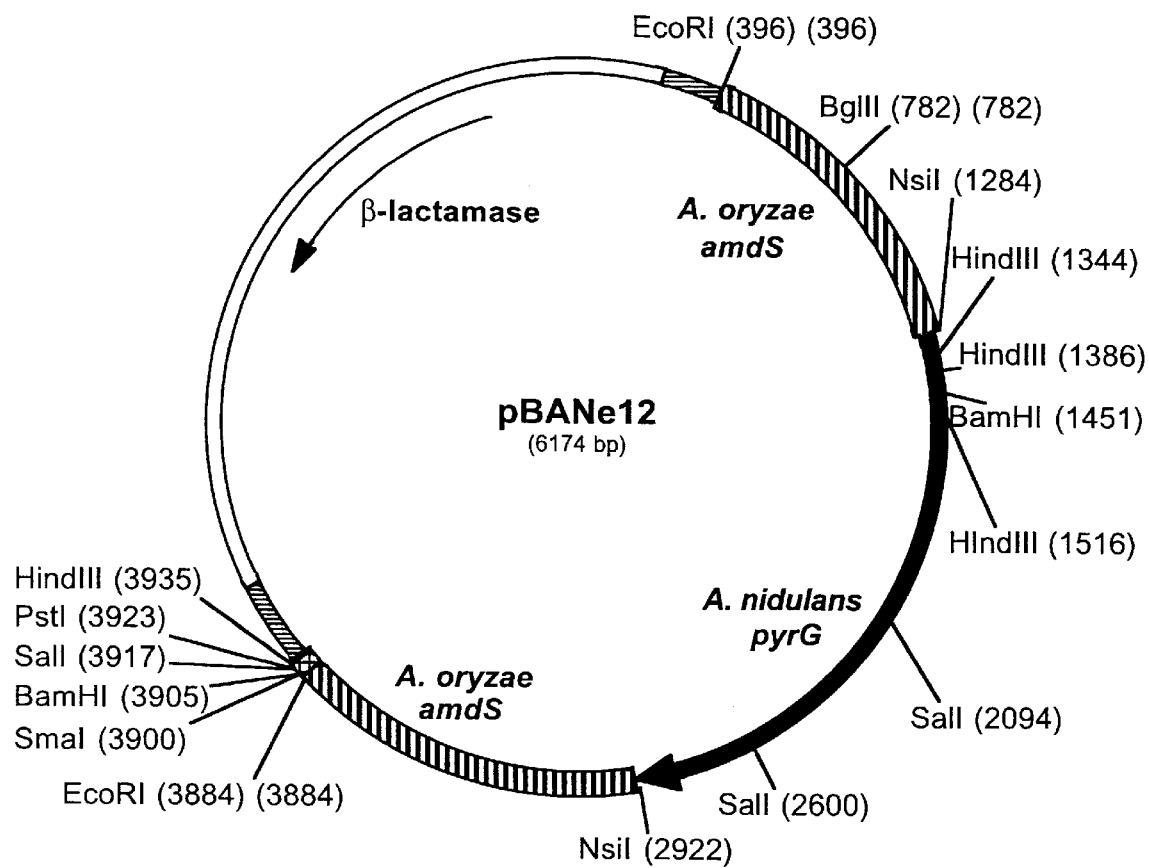
FIG. 11 shows a restriction map of pBANe12.

In order to obtain a cassette for the disruption of the amdS locus of Aspergillus oryzae, an 800 bp NsiI fragment within the amdS gene was deleted and replaced by the Aspergillus nidulans pyrG gene as follows. The amdS gene was excised from the pCRII vector by digesting with EcoRI and subsequently subcloned into pUC118 to generate pBANe11 (FIG. 10).

pUC4-AN.pyrG1&2 was digested with NsiI and a 1.6 kb fragment containing the pyrG gene was isolated by 1% agarose gel electrophoresis using TAE buffer and then purified using a FMC SpinBind Kit. The purified fragment was ethanol precipitated and resuspended in 30 µl of TE. To disrupt the amdS gene, pBANe11 was digested with NsiI to excise the 800 bp fragment and the 1.6 kb Aspergillus nidulans pyrG gene was inserted to generate pBANe12 (FIG. 11). pBANe12 was linearized by digesting with EcoRI and the fragment was purified using a FMC SpinBind Kit. This linear fragment was used to transform Aspergillus oryzae HowB425.

Aspergillus oryzae HowB425 was grown in 150 ml of YEG medium at 34° C. for 16–18 hours with agitation at 130 rpm. The mycelia were recovered by filtration through a 0.2 µm filter until approximately 10 ml remained on the filter, washed with approximately 50 ml of 1 M $MgSO_4.7H_2O$ (0.2 µm filtered), and then collected with a sterile spatula and placed in a 125 ml Ehrlenmeyer flask. The mycelia were then resuspended with 5 mg/ml of NOVOZYM 234™ (Novo Nordisk A/S, Bagsvaerd, Denmark) in 20 ml of 1 M $MgSO_4.7H_2O$. The suspension was incubated at 34° C. with gentle agitation at 80 rpm for approximately 30 minutes to generate protoplasts.

The contents of the 125 ml Ehrlenmeyer flask was then filtered through sterile Miracloth into a 30 ml polypropylene centrifuge tube and Miracloth washed with 20 ml of 2 M sorbitol. The tube was capped, mixed gently, and centrifuged at 3000×g for 15 minutes in a swinging bucket Sorval RT6000 rotor to recover the protoplasts. The supernatant was removed and the protoplasts were resuspended in 1 ml of 1 M sorbitol. The volume was then raised to 30 ml with 1 M sorbitol and centifuged at 2000×g for 10 minutes. The wash was repeated using STC (1.2 M sorbitol-10 mM Tris-10 mM $CaCl_2.2H_2O$ pH 7.5). The protoplasts were resuspended in STC to a final concentration of $2×10^7$ protoplasts per ml.

Transformation of Aspergillus oryzae HowB425 was conducted with protoplasts at a concentration of $2×10^7$ protoplasts per ml. One hundred µl of protoplasts were placed on ice for 30 minutes with 5 µg of the EcoRI fragment from pBANe12. One ml of SPTC (40% polyethylene glycol 4000–0.05 M $CaCl_2$-0.8 M sorbitol-0.05 M Tris pH 8.0) was added and the protoplasts were incubated at 37° C. for 20 minutes. Five ml of STC were added to each transformation prior to plating 3 ml each onto either Minimal Medium or Acetate Medium with fluoroacetamide. Plates were incubated 5 to 7 days at 37° C. Colonies were picked with sterile toothpicks to plates of the same medium. Colonies were purified by streaking spores and picking isolated colonies. Forty-seven and sixty-five transformants were obtained on the Minimal Medium or Acetate Medium plates, respectively. Colonies were transferred to the same type of medium that they initially grew on for spore purification.

Spores of putative transformants were grown in 25 ml of YEG medium overnight at 37° C. Mycelia was filtered through Miracloth and rinsed three times with distilled water. Extra water was squeezed out and the mycelia was frozen in liquid nitrogen and ground into a fine powder using a mortar and pestle. The Purgene DNA Isolation Kit (Gentra Systems Inc., Minneapolis, Minn.) was used to isolate genomic DNA from each transformant. Thirty-one transformants were screened by PCR using Primers 15 and 16 shown above using the same method as described above except the reactions were incubated for one cycle at 95° C. for 5 minutes followed by 25 cycles each at 94° C. for 1 minute, 55° C. for 1 minute, and 72° C. for 2 minutes. The untransformed control produced a 2.66 kb band. Three of the transformants gave the expected size (3370 bp) PCR product for a disruption of amdS.

The three putative ΔamdS strains were analyzed by Southern blot to confirm the amdS locus had been disrupted Two µg of genomic DNA from putative ΔamdS strains was digested with 10 µl of 1×buffer for each of the restriction enzymes SalI, EcoRI, NotI, BamHI, and HindIII for 24 hours at 37° C. The digested DNA was electrophoresed using a 0.6% agarose gel (SeaKem Gold, FMC, Rockland, Me.) with TAE buffer. The gel was denatured, neutralized, and soaked in 20×SSC of 30 minutes at each step. The digested DNA was transferred for 16 hours onto a Nytran membrane (Schleicher & Schuell, Keene, NH) using a Schleicher & Schuell TurboBlotter (Keene, N.H). The membrane was rinsed in 2×SSC and the DNA was UV stratalinked using UV Stratalinker 2400 (Stratagene Cloning Systems, La Jolla, Calif.). The Genius System (Boehringer Mannheim, Indianapolis, Ind.) was used to probe the membranes. The membrane was prehybridized using 20 ml of Easy Hyb at 42° C. for 1 hour. The amdS probe was DIG labeled using pBANe11 DNA, oligonucleotides 1 and 2, 5 U of Taq DNA polymerase, and the Boehringer Mannheim Dig DNA label mix (Boehringer Mannheim, Indianapolis, Ind.). The probe was quantified and added at 1 ng/ml after it was denatured. The membrane was probed overnight at 42° C. The probe was decanted and the membrane was washed twice for 5 minutes in 2×SSC; 0.1% SDS at room temperature and twice for 15 minutes in 0.1×SSC; 0.1% SDS at 65° C. Detection of DIG-labeled nucleotides was done by following the protocol provided by Boehringer Mannheim using Lumi-Phos 530. Membranes were exposed to film for 15 minutes.

Southern analysis indicated that two of the strains, Aspergillus oryzae BANe1 and BANe2, appeared to have multiple copies of the disruption cassette integrated at the amdS locus where two flanking regions and a tandem repeat at the 3500 bp position were observed when the DNA was digested with BamHI and HindIII. Aspergillus oryzae BANe3 appeared to be a clean disruption in which one copy of the disruption cassette had been integrated at the amdS locus. Aspergillus oryzae BANe3 had only two expected bands of 5.2 kb and 3.5 kb when digested with BamHI and 6 kb and 3.8 kb when digested with HindIII.

Example 5

Transformation of Aspergillus oryzae BANe3

Aspergillus oryzae BANe3 was grown in 100 ml of YEG medium at 34° C. for 16–18 hours with agitation at 160 rpm. The mycelia were recovered by filtration through a 0.2 µm filter until approximately 10 ml remained on the filter, washed with approximately 20 ml of 1 M $MgSO_4.7H_2O$ (0.2 µm filtered), and then collected with a sterile loop and placed in a 125 ml Ehrlenmeyer flask. The mycelia were then resuspended with 75 mg of NOVOZYM 234™ (Novo Nordisk A/S, Bagsvaerd, Denmark) in 15 ml of 1 M MgSO$_4$.7H$_2$O. The suspension was incubated at 37° C. with gentle agitation at 50 rpm for approximately one hour to generate protoplasts.

The contents of the 125 ml Ehrlenmeyer flask was then filtered through sterile. Miracloth into a 30 ml Corex centrifuge tube, overlaid with 6 ml of 0.6 M sorbitol-100 mM Tris pH 7.0, and centrifuged at 3500×g for 15 minutes in a swinging bucket rotor to recover the protoplasts. The protoplasts were recovered from the buffer interface with a Pasteur pipet. The protoplasts were then washed with two volumes of STC (1.2 M sorbitol-10 mM Tris-10 mM CaCl$_2$.2H$_2$O pH 7.5) and centrifuged at 3500×g for 5 minutes. The protoplasts were washed two times in 10 ml of STC and centrifuged as before. The protoplasts were resuspended in STC to a final concentration of 1.7×10$^7$ protoplasts per ml.

Transformation of *Aspergillus oryzae* BANe3 for amdS selection was conducted with protoplasts at a concentration of 1.7×10$^7$ protoplasts per ml. Ten µg of DNA (pDBEL1, pDBEL1T, pDBEL1C, or pDBEL1G) were added to 100 µl of protoplasts followed by 250 µl of PEG solution (60% PEG 4000–10 mM CaCl$_2$). The mixture was placed at 37° C. for 30 minutes. Four ml of STC was then added and the mixture was plated onto COVE plates selecting for amdS. The plates were incubated 5–7 days at 37° C. The transformants were purified by streaking spores and picking isolated colonies from COVE plates incubated at 37° C.

Example 6

Analysis of Transformants for Lipase Production

The *Aspergillus oryzae* BANe3 transformants obtained in Example 5 were assayed for lipase expression. For microtiter assays, MY25 medium was diluted 100 fold with 49% glass distilled water and 50% 2×MY Salts pH 6.5 solution. A volume of 1.25 ml of 1/100 strength MY25 medium was added to the wells of a 24 well cell culture plate. The wells were inoculated with 10 µl of spores from each transformant, and the plates were incubated at 34° C. with agitation at 100 rpm. Each transformant was inoculated into three wells. Untransformed *Aspergillus oryzae* BANe3 was used to inoculate three wells.

Samples of 100 µl were removed on days 3 and 5 from each well of the 24 well cell culture plates. Each sample was diluted with 200 µl of 100 mM alpha olefin sulfonate (AOS) detergent in 4 mM CaCl$_2$-100 mM MOPS pH 7.5 (MC buffer) and 20 µl aliquots were dispensed to wells in 96-well plates followed by 200 µl of diluted substrate. The lipase assay substrate was prepared by diluting 1:50 a p-nitrophenylbutyrate stock substrate (21 µl of p-nitrophenylbutyrate/ml DMSO) into MC buffer immediately before use. Standard lipase (LIPOLASE™, Novo Nordisk A/S, Bagsvaerd, Denmark) was prepared to contain 40 LU/ml of MC buffer containing 0.02% AOS detergent. The standard was stored at 4° C. until use. Standard lipase was diluted 1/40 in MC buffer just before use. Using a plate reader, the absorbance at 405 nm was recorded as the difference of two readings taken at approximately 1 minute intervals. Lipase units/ml (LU/ml) were calculated relative to the lipase standard. The results of the lipase assays are shown in Table I relative to lipase activity obtained with pDBEL1.

TABLE I

Lipase Expression by *Aspergillus oryzae* BANe3 transformants

| Plasmid DNA | # Transformants screened | Relative Mean lipase (LU/ml) | Relative Median lipase (LU/ml) |
|---|---|---|---|
| pDBEL1 | 46 | 1 | 1 |
| pDBEL1G | 46 | 0.91 | 0.87 |
| pDBEL1C | 47 | 0.57 | 0.42 |
| pDBEL1T | 50 | 0.31 | 0 |

As shown in Table I, lipase expression was highest when the *Humicola lanuginosa* lipase gene contained a purine at the minus 3 position with the highest expression when the minus 3 position contained an A nucleotide. When the minus 3 position contained a pyrimidine, lipase expression dropped significantly with the lowest expression when the minus 3 position contained a T nucleotide.

Example 7

Construction of pJaL485 and its Variants pJaL485 (FIG. 12) was constructed to contain the truncated niaD gene and an expression cassette where the *Humicola lanuginosa* lipase gene was sandwiched between the NA2 promoter and the *Aspergillus niger* AMG terminator.

Plasmid pSTA14 encoding the *Aspergillus oryzae* niaD gene (Unkles et al,. 1989, *Molecular General Genetics* 218: 99–104) was digested with HindIII and the 5136 bp fragment was purified and cloned into pUC19 digested with HindIII to yield plasmid pToC108. Plasmid pToC108 was digested with BglII-SalI and the 3700 bp fragment was purified and cloned into pUC19 digested with BglII-SalI to yield plasmid pJaL410. This plasmid is encoding a truncated niaD gene wherein the 85 N-terminal amino acids has been removed.

Plasmid pJaL410 was digested with SacI-PstI and treated with Klenow and dNTP's and the 6018 bp fragment was purified and religated to yield plasmid pJaL420. The BamHI site in pJaL420 was removed by making a silent mutation by using the Chameleon Double-Stranded Site-Directed Mutagenesis Kit (Stratagene Cloning Systems, La Jolla, Calif.) according to the manufacturer's instructions giving plasmid pJaL423. The BamHI site was destroyed by changing the T in the BamHI site to a C using the following primer:

5'-GGAACGATGGACCCGGAAGGTTTAAAAGC-3' (SEQ ID NO. 28)

Sequencing around the destroyed BamHI site revealed that further downstream there was some unexpected changes which resulted in a frame shift in the niaD gene and the creation of a SmaI site. To repair this frame shift the 291 bp AccI-DraI fragment in pJaL423 was exchanged with the corresponding fragment from pJaL420 to give pJaL475.

Figure 12:
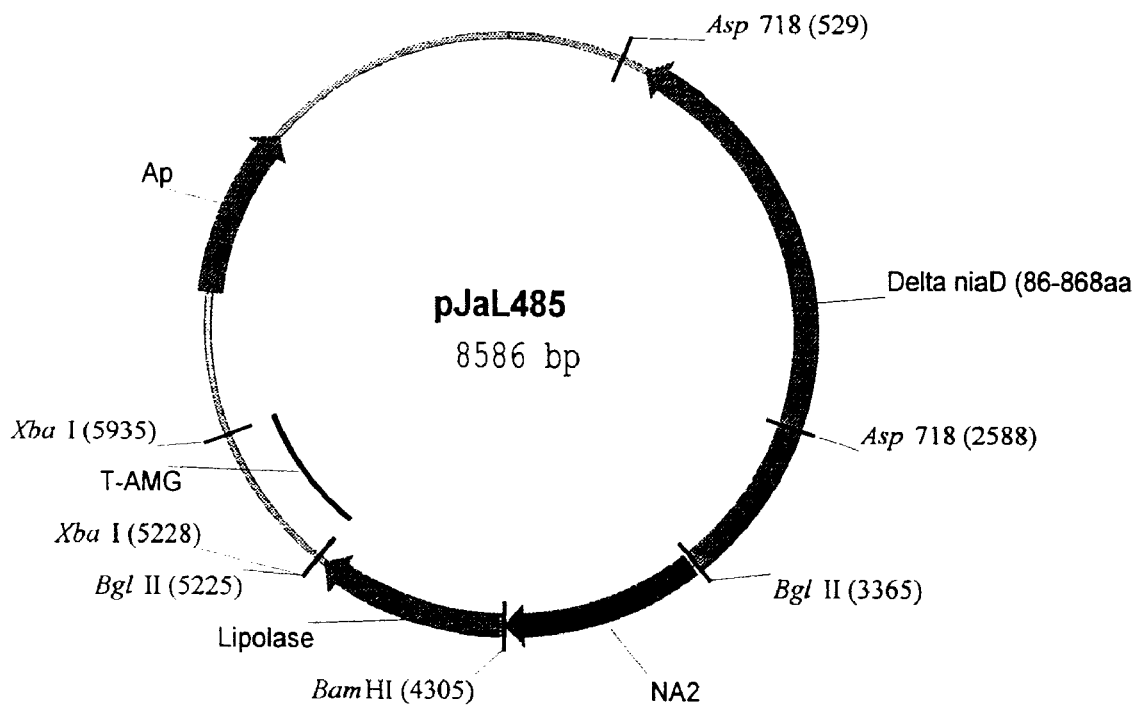
FIG. 12 shows a restriction map of pJaL485.

The 3381 bp HindIII fragment from pJaL475 encoding the truncated niaD gene was cloned into the HindIII site of plasmid pJaL211, resulting in plasmid pJaL479. The HindIII site at position 2 was destroyed by partial digestion with HindIII followed by treatment with Klenow and dNTP's. The 8586 bp fragment was purified and religated to yield plasmid pJaL485 (FIG. 12).

The nucleotide sequence upstream of the *Humicola lanuginosa* lipase gene in pJaL485 is GGGATCCACCATG (SEQ ID NO. 29) with the minus 3 position containing an A nucleotide.

Six variants of pJaL485 were produced by changing the nucleotide sequence upstream of the *Humicola lanuginosa* lipase gene using the Stratagene QuikChange™ Site-Directed Mutagenesis Kit according to the manufacturer's instructions and the primers listed below.

Primer 17:
5'-CCCCACAGAAGGGATCCACTATGAGGAGC TCCCTTG-3' (SEQ ID NO. 30)

Primer 18:
5'-CAAGGGAGCTCCTCATAGTGGATCCCTTCT cGTGGGG-3' (SEQ ID NO. 31)

Primer 19:
5'-CCCCACAGAAGGGATCCATCATGAGGAGCT CCCTTG-3' (SEQ ID NO. 32)

Primer 20:
5'-CAAGGGAGCTCCTCATGATGGATCCCTTCT GTGGGG-3' (SEQ ID NO. 33)

Primer 21:
5'-CCCCACAGAAGGGATCCTCCATGAGGAGC TCCCTTG-3' (SEQ ID NO. 34)

Primer 22:
5'-CAAGGGAGCTCCTCATGGAGGATCCCTTCT GTGGGG-3' (SEQ ID NO. 35)

Primer 23:
5'-CCCCACAGAAGGGATCTACCATGAGGAGC TCCCTTG-3' (SEQ ID NO. 36)

Primer 24:
5'-CAAGGGAGCTCCTCATGGTAGATCCCTTCT GTGGGG-3' (SEQ ID NO. 37)

Primer 25:
5'-CCCCACAGAAGGGATCTTTTATGAGGAGCT CCCTTG-3' (SEQ ID NO. 38)

Primer 26:
5'-CAAGGGAGCTCCTCATAAAAGATCCCTTCT GTGGGG-3' (SEQ ID NO. 39)

Primer 27:
5'-CCCCACAGAAGTCCTTCACCATGAGGAGC TCCCTTG-3' (SEQ ID NO. 40)

Primer 28:
5'-CAAGGGAGCTCCTCATGGTGAAGGACTTC TGTGGGG-3' (SEQ ID NO. 41)

Primers 17 and 18 were used to construct pDBEL2-1T which differs from pJaL485 only at the minus 1 position of the *Humicola lanuginosa* lipase gene. pJaL485 contains a C nucleotide at this position while pDBEL2-1T contains a T nucleotide.

Primers 19 and 20 were used to construct pDBEL2-2T which differs from pJaL485 only at the minus 2 position of the *Humicola lanuginosa* lipase gene. pJaL485 contains a C nucleotide at this position while pDBEL2-2T contains a T nucleotide.

Primers 21 and 22 were used to construct pDBEL2-3T which differs from pJaL485 only at the minus 3 position of the *Humicola lanuginosa* lipase gene. pJaL485 contains an A nucleotide at this position while pDBEL2-2T contains a T nucleotide.

Primers 23 and 24 were used to construct pDBEL2-4T which differs from pJaL485 only at the minus 4 position of the *Humicola lanuginosa* lipase gene. pJaL485 contains a C nucleotide at this position while pDBEL2-4T contains a T nucleotide.

Primers 25 and 26 were used to construct pDBEL2-1-4T which differs from pJaL485 only at the minus 4 to minus 1 positions of the *Humicola lanuginosa* lipase gene. pJaL485 contains the nucleotides CACC in these positions while pDBEL2-1-4T contains the nucleotides TTTT.

Primers 27 and 28 were used to construct pDBEL3 which differs from pJaL485 only at the positions minus 9 to minus 7 and at position minus 5 of the *Humicola lanuginosa* lipase gene. pJaL485 contains a C nucleotide at the minus 5 position and nucleotides GGA at positions minus 9 to minus 7 while pDBEL3 contains nucleotides TCC at positions minus 9 to minus 7 and a T nucleotide at the minus 5 position.

The PCR reactions were incubated in a Perkin Elmer 9600 Thermocycler programmed as follows: One cycle at 95° C. for 30 seconds followed by 12 cycles each at 95° C. for 30 seconds, 55° C. for 1 minute, and 68° C. for 14 minutes. PCR reactions were treated with 10 units Dpn I to digest the non-mutated parental DNA. The digest reactions were then used to transform *E. coli* XL1-Blue supercompetent cells following the Stratagene QuikChange™ Site-Directed Mutagenesis kit protocol.

The nucleotide sequence of the pJaL485 variants (pDBEL2-1T, pDBEL2-2T, pDBEL2-3T, pDBEL2-4T, pDBEL2-1-4T, and pDBEL3) was determined using Taq DNA polymerase cycle-sequencing with fluorescent labeled nucleotides. The sequencing reactions were electrophoresed on an Applied Biosystems Automatic DNA Sequencer (Model 377, version 3.0). The sequencing primers listed above (971308 and 971309) were used for sequencing of the pJaL485 variants.

Example 8

Construction of *Aspergillus oryzae* JaL294

For construction of a defined *Aspergillus oryzae* niaD mutant a replacement plasmid pJaL448 (FIG. 13) was constructed where the C-terminal part of the niaD gene was replaced by the *Aspergillus oryzae* pyrG gene.

Figure 13:
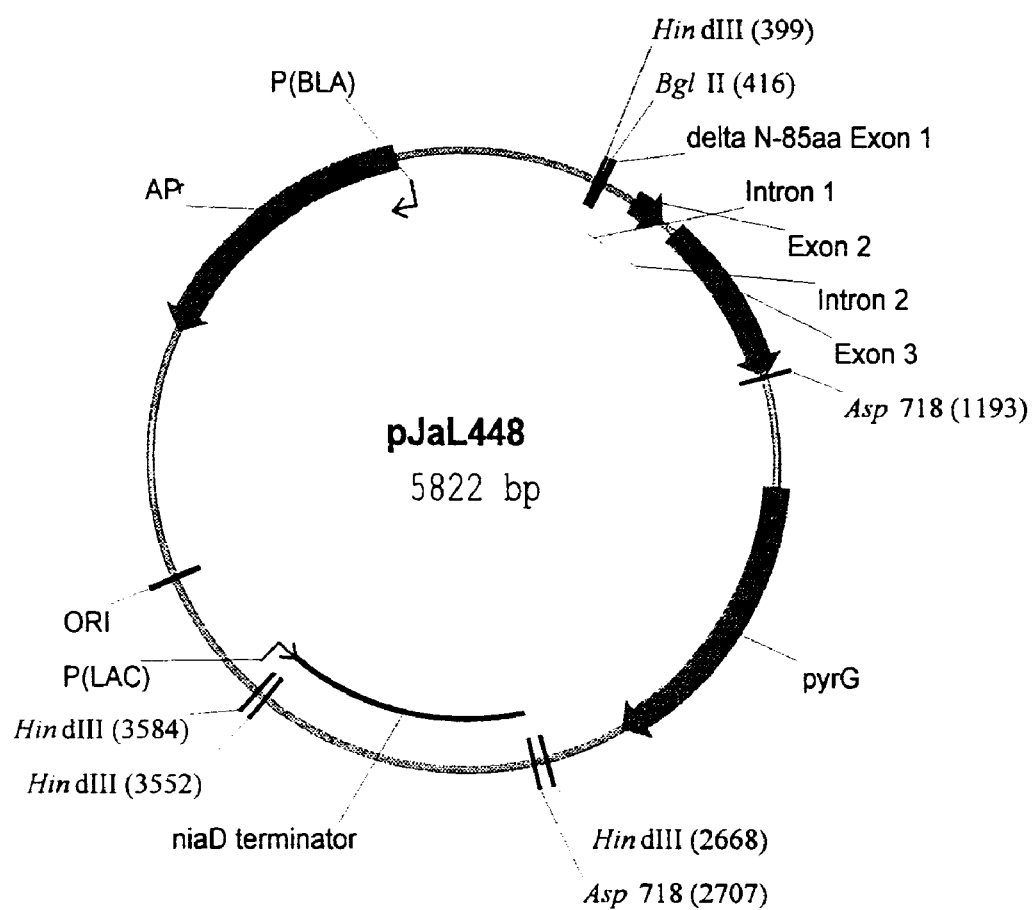
FIG. 13 shows a restriction map of pJaL448.

Plasmid pJaL410 (construction described in Example 7) was digested with KpnI and the 4307 bp fragment was purified and religated to yield plasmid pJaL419. Plasmid pJeRS4 (U.S. Pat. No. 5,861,280) encoding the *Aspergillus oryzae* pyrG gene was digested with KpnI and the 1515 bp fragment was purified and ligated with pJaL419 digested with KpnI to yield pJaL448 (FIG. 13).

Plasmid pJaL448 is a double cross-over plasmid where the *Aspergillus oryzae* pyrG gene (1515 bp KpnI fragment from pJeRS4) is flanked by a 782 bp BglII-KpnI fragment encoding amino acid 85 to 276 of the niaD protein and by a 841 bp KpnI-HindIII fragment containing the niaD terminator.

Protoplasts of *Aspergillus oryzae* JaL250 were prepared using the same protocol as described in Example 5. pJaL448 was linearized with XhoI and transformed into protoplasts of *Aspergillus oryzae* JaL250 (apyrG derivative of *Aspergillus oryzae* JaL228). Transformation of *Aspergillus oryzae* JaL250 for chlorate resistance selection was conducted with protoplasts at a concentration of $1.7 \times 10^7$ protoplasts per ml. Ten µg of linearized pJaL448 were added to 100 µl of protoplasts. A volume of 250 µl of PEG solution (60% PEG 4000–10 mM $CaCl_2$) was then added and the mixture was placed at 37° C. for 30 minutes. Four ml STC was then added and the mixture was plated onto Minimal media plates selecting for chlorate resistance. The plates were incubated 5–7 days at 37° C. Chlorate resistance transformants (9 out of 45) were isolated and further purified on chlorate-containing minimal medium with glutamate as the sole source of nitrogen. The ability of these 9 mutants to grow on nitrate and nitrite as sole nitrogen source was assessed. Three had a phenotype indicative of nitrate reductase structural mutants (niaD), i.e., they failed to grow with nitrate but grew on nitrite as sole nitrogen source.

Southern analysis of BamHI-, KpnI-, and HindIII-digested genomic DNA from the three mutant strains, probed with either the 2 kb KpnI fragment or with the 3.7 kb HindIII fragment from pJaL410, demonstrated that only one of the transformants, designated *Aspergillus oryzae* JaL294, has the expected gene replacement at the niaD locus as shown in FIG. 12.

Example 9

Transformation of *Aspergillus oryzae* JaL294

Protoplasts of *Aspergillus oryzae* JaL294 were prepared using the same protocol as described in Example 5.

Transformation of *Aspergillus oryzae* JaL294 for niaD selection was conducted with protoplasts at a concentration of $1.7 \times 10^7$ protoplasts per ml. Ten µg of DNA (pDBEL2-1T, pDBEL2-2T, pDBEL2-3T, pDBEL2-4T, pDBEL2-1-4T, pDBEL3, or pJaL485) were added 100 µl of protoplasts. A volume of 250 µl of PEG solution (60% PEG 4000–10 mM $CaCl_2$) was then added and the mixture was placed at 37° C. for 30 minutes. Four ml STC was then added and the mixture was plated onto Minimal media plates selecting for niaD. The plates were incubated 5–7 days at 37° C. The transformants were purified by streaking spores and picking isolated colonies from Minimal media plates incubated at 37° C.

Example 10

Characterization of Integration Events in *Aspergillus oryzae* JaL294 Transformants Genomic DNA was isolated from all of the *Aspergillus oryzae* JaL294 transformants according to the following procedure. Each transformant was grown in 5 ml of YEG medium for 24 hours at 37° C. in a small Petri plate (60×15 mm). Mycelia were then collected from each culture by filtration through Whatman filter paper No. 1 (Whatman, Springfield Mill, England) and transferred to a 1.7 ml centrifuge tube. The mycelia preparations were frozen in liquid nitrogen and dried in a SpeedVac (Savant Instruments, Inc., Farmingdale, N.Y.) for 1.5 hours. The frozen mycelia preparations were ground to a fine powder with a sterile toothpick. A Qiagen DNeasy Kit (QIAGEN, Inc., Valencia, Calif.) was used to extract the genomic DNA from the frozen mycelia following the manufacturer's instructions.

The genomic DNA was digested with PstI and then Southern hybridization was used to determine whether there was a single copy of the plasmid integrated into the transformants according to the procedure described by Sambrook et al., 1989, supra. Additionally, genomic DNA was extracted from untransformed *Aspergillus oryzae* JaL294. Southern blots of the digests were probed with a 0.834 kb niaD fragment obtained from pJaL485. The fragment was labeled with dioxygenin using a Boehringer Mannheim PCR DIG Probe Synthesis Kit (Boehringer Mannheim, Indianapolis, Ind.) according to the manufacturer's instructions. The blot was prehybridized for 2 hours and hybridized overnight at 50° C. in DIG Easy Hyb. The blot was washed and processed as recommended by the manufacturer.

The Southern blot demonstrated that pJaL485 contained a 8.5 kb band and untransformed *Aspergillus oryzae* JaL294 contained a 5.7 kb band when probed with the niaD fragment. Transformants in which a single copy of the plasmid was integrated should contain a 11.7 kb and 2.6 kb bands. Transformants in which multiple copies of the plasmid were integrated should contain the same 11.7 kb and 2.6 kb bands as well as a third band of 8.5 kb. Those transformants which had integrated a single copy of the plasmid DNA were then grown in shake flask and subsequently assayed for lipase expression.

Example 11

Analysis of Transformants in Shake Flask

The *Aspergillus oryzae* transformants were cultivated by inoculating 170 µl of a spore suspension (0.01% Tween-80 plus spores from Minimal media plates) into 25 ml of MY25 medium at pH 6.5 into a 125 ml polypropylene shake flask and incubating the shake flasks at 34° C. with agitation at 225 rpm. Samples were taken at days 3 and 5 and lipase activity was measured as described in Example 5.

Table 2 shows the nucleotide sequence in positions minus 9 to plus 3 for pJaL485 and all its variants. The results obtained are shown in Table 3 below relative to lipase activity obtained with pJaL485.

TABLE 2

Nucleotide sequence in positions minus 9 to plus 3

| Plasmid | Nucleotide sequence | |
|---|---|---|
| pJa1485 | 5'-GGATCCACCATG-3' | (SEQ ID NO.42) |
| pDBEL2-1 | 5'-GGATCCACTATG-3' | (SEQ ID NO.43) |
| pDBEL2-2 | 5'-GGATCCATATG-3' | (SEQ ID NO.44) |
| pDBEL2-3 | 5'-GGATCCTCCATG-3' | (SEQ ID NO.45) |
| pDBEL2-4 | 5'-GGATCTACCATG-3' | (SEQ ID NO.46) |
| pDBEL2-1-4 | 5'-GGATCTTTTATG-3' | (SEQ ID NO.47) |
| pDBEL3 | 5'-TCCTTCACCATG-3' | (SEQ ID NO.48) |

TABLE 3

Lipase expression by *Aspergillus oryzae* JaL294 transformants

| Plasmid DNA | # Transformants screened | Relative Mean lipase (LU/ml) | Median lipase (LU/ml) |
|---|---|---|---|
| pJaL485 | 3 | 1 | 1 |
| pDBEL2-1 | 5 | 0.94 | 0.94 |
| pDBEL2-2 | 5 | 0.94 | 0.89 |
| pDBEL2-3 | 8 | 0.36 | 0.35 |
| pDBEL2-4 | 7 | 0.95 | 0.92 |
| pDBEL2-1-4 | 6 | 0.07 | 0.07 |
| pDBEL3 | 6 | 1.66 | 1.65 |

As shown in Table 3 when the nucleotides in positions minus 1, minus 2, or minus 4 were changed to a T nucleotide (pDBEL2-1, pDBEL2-2, and pDBEL2-4), there was no significant change in expression of lipase as compared to the wild type plasmid (pJaL485). When the nucleotide in the minus 3 position was changed from an A nucleotide (pJaL485) to a T nucleotide (pDBEL2-3) there was a significant decrease in lipase expression. However, when all the nucleotides in positions minus 4 to minus 1 were changed to a T nucleotide (pDBEL2-1-4) there was a further decrease in expression of lipase beyond what was seen when only a single nucleotide was changed at any of the positions. pDBEL3 contained the Aspergillus consensus sequence in positions minus 9 to minus 1. This resulted in a significant increase in lipase expression.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

What is claimed is:

1. A method for producing a polypeptide, comprising:
(a) cultivating a fungal host cell in a medium conducive for the production of the polypeptide, wherein the fungal host cell comprises a first nucleic acid sequence encoding the polypeptide operably linked to a second nucleic acid sequence comprising a consensus translational initiator sequence foreign to the first nucleic acid sequence wherein the 3' end of the consensus translational initiator sequence is immediately upstream of the initiator codon of the first nucleic acid sequence, and the consensus translational initiator sequence comprises the sequence 5'-NYCNNHCACC-3' (SEQ ID NO:1) wherein N is a nucleotide selected from the group consisting of adenine (A), guanine (G), cytosine (C), and thymine (T); Y is a cytosine (C) or thymine (T); and H is a nucleotide selected from the group consisting of adenine (A), cytosine (C), and thymine (T); and
(b) isolating the polypeptide from the cultivation medium.

2. The method of claim 1, wherein the consensus translational initiator sequence comprises the nucleic acid sequence of SEQ ID NO:2.

3. The method of claim 1, wherein the consensus translational initiator sequence comprises the nucleic acid sequence of SEQ ID NO:3.

4. The method of claim 1, wherein the consensus translational initiator sequence comprises the nucleic acid sequence of SEQ ID NO:4.

5. The method of claim 1, wherein the fungal host cell contains one or more copies of the first nucleic acid sequence.

6. The method of claim 1, wherein the fungal host cell contains one copy of the first nucleic acid sequence.

7. The method of claim 1, wherein the first nucleic acid sequence encodes a polypeptide heterologous to the fungal host cell.

8. The method of claim 1, wherein the polypeptide is hormone or hormone variant, enzyme, receptor or portion thereof, antibody or portion thereof, or reporter.

9. The method of claim 1, wherein the first and second nucleic acid sequences are contained in the chromosome of the fungal host cell.

10. The method of claim 1, wherein the first and second nucleic acid sequences are contained on an extrachromosomal element.

11. The method of claim 1, wherein the fungal host cell is a filamentous fungal or yeast cell.

12. The method of claim 1, wherein the fungal host cell produces at least about 25% more polypeptide relative to a fungal cell containing a non-consensus translational initiator sequence operably linked to a nucleic acid sequence encoding the polypeptide when cultured under identical production conditions.

13. The method of claim 8, wherein the enzyme is an oxidoreductase, transferase, hydrolase, lyase, isomerase, or ligase.

14. The method of claim 13, wherein the enzyme is an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, invertase, laccase, lipase, mannosidase, mutanase, oxidase, a pectinolytic enzyme, peroxidase, phytase, polyphenoloxidase, proteolytic enzyme, ribonuclease, transglutaminase, or xylanase.

15. The method of claim 11, wherein the filamentous fungal cell is an Acremonium, Aspergillus, Fusarium, Humicola, Mucor, Myceliophthora, Neurospora, Penicillium, Thielavia, Tolypocladium, or Trichoderma cell.

16. The method of claim 11, wherein the yeast cell is a Candida, Hansenula, Kluyveromyces, Pichia, Saccharomyces, Schizosaccharomyces, or Yarrowia cell.

17. The method of claim 11, wherein the filamentous fungal host cell is an Aspergillus cell.

18. The method of claim 11, wherein the filamentous fungal host cell is a Fusarium cell.

19. An isolated consensus translational initiator sequence comprising the sequence 5'-NYCNNHCACC-3' (SEQ ID NO:1), wherein N is a nucleotide selected from the group consisting of adenine (A), guanine (G), cytosine (C), and thymine (T); Y is a cytosine (C) or thymine (T); and H is a nucleotide selected from the group consisting of adenine (A), cytosine (C), and thymine (T).

20. The isolated consensus translational initiator sequence of claim 19, wherein the consensus translational initiator sequence comprises the nucleic acid sequence of SEQ ID NO:2.

21. The isolated consensus translational initiator sequence of claim 19, wherein the consensus translational initiator sequence comprises the nucleic acid sequence of SEQ ID NO:3.

22. The isolated consensus translational initiator sequence of claim 19, wherein the consensus translational initiator sequence comprises the nucleic acid sequence of SEQ ID NO:4.

23. A nucleic acid construct comprising a nucleic acid sequence encoding a polypeptide operably linked to the consensus translational initiator sequence of claim 19.

24. A recombinant expression vector comprising the nucleic acid construct of claim 23.

25. A recombinant host cell comprising the recombinant expression vector of claim 24.

\* \* \* \* \*